US008809350B2

(12) United States Patent
Benigni et al.

(10) Patent No.: US 8,809,350 B2
(45) Date of Patent: Aug. 19, 2014

(54) PURINE AND PYRIMIDINE CDK INHIBITORS AND THEIR USE FOR THE TREATMENT OF AUTOIMMUNE DISEASES

(75) Inventors: Ariela Benigni, Bergamo (IT); Carla Zoja, Bergamo (IT); Giuseppe Remuzzi, Bergamo (IT); Athos Gianella-Borradori, Gauting (DE)

(73) Assignee: Cyclacel Limited, London (GB)

( * ) Notice: Subject to any disclaimer, the term of this patent is extended or adjusted under 35 U.S.C. 154(b) by 0 days.

(21) Appl. No.: 13/464,362

(22) Filed: May 4, 2012

(65) Prior Publication Data

US 2012/0309723 A1 Dec. 6, 2012

Related U.S. Application Data

(63) Continuation of application No. 11/660,249, filed as application No. PCT/GB2005/003350 on Aug. 25, 2005, now abandoned.

(30) Foreign Application Priority Data

Aug. 27, 2004 (GB) .................................. 0419175.5
Aug. 27, 2004 (GB) .................................. 0419176.3

(51) Int. Cl.
*A61K 31/52* (2006.01)
*A61K 31/573* (2006.01)

(52) U.S. Cl.
CPC ............... *A61K 31/52* (2013.01); *A61K 31/573* (2013.01)
USPC ......... 514/263.4; 514/171; 514/179; 514/181

(58) Field of Classification Search
CPC ........................... A61K 31/52; A61K 31/573
USPC ............................ 514/263.4, 171, 179, 181
See application file for complete search history.

(56) References Cited

U.S. PATENT DOCUMENTS

| | | | |
|---|---|---|---|
| 5,424,400 A | 6/1995 | Smith | |
| 5,516,775 A | 5/1996 | Zimmermann et al. | |
| 5,596,079 A | 1/1997 | Smith et al. | |
| 5,624,819 A | 4/1997 | Skolnick et al. | |
| 5,672,508 A | 9/1997 | Gyuris et al. | |
| 5,739,027 A | 4/1998 | Kamb | |
| 5,807,692 A | 9/1998 | Kinzler et al. | |
| 5,866,702 A | 2/1999 | Mackman et al. | |
| 6,107,301 A | 8/2000 | Aldrich et al. | |
| 6,316,456 B1 * | 11/2001 | Meijer et al. | 514/263.4 |
| 6,552,192 B1 | 4/2003 | Hanus et al. | |
| 2003/0229105 A1 | 12/2003 | Kashanchi | |
| 2004/0063715 A1 * | 4/2004 | Paruch et al. | 514/249 |
| 2004/0097516 A1 * | 5/2004 | Dwyer et al. | 514/253.04 |

FOREIGN PATENT DOCUMENTS

| | | |
|---|---|---|
| DE | 10127581 A1 | 1/2003 |
| EP | 0002805 B1 | 7/1979 |
| EP | 0164204 A1 | 12/1985 |
| EP | 0233461 B1 | 8/1987 |
| EP | 0475623 B1 | 3/1992 |
| EP | 0518650 B1 | 12/1992 |
| EP | 0739341 B1 | 10/1996 |
| FR | 2662698 A1 | 12/1991 |
| WO | 91/18981 A2 | 12/1991 |
| WO | 92/00757 A1 | 1/1992 |
| WO | 93/12251 A1 | 6/1993 |
| WO | 94/02167 A1 | 2/1994 |
| WO | 94/09135 A1 | 4/1994 |
| WO | 95/06415 A1 | 3/1995 |
| WO | 95/09847 A1 | 4/1995 |
| WO | 95/09852 A1 | 4/1995 |
| WO | 95/13375 A1 | 5/1995 |
| WO | 95/16771 A1 | 6/1995 |
| WO | 95/19358 A1 | 7/1995 |
| WO | 95/28483 A1 | 10/1995 |
| WO | 95/31995 A1 | 11/1995 |
| WO | 95/35115 A1 | 12/1995 |
| WO | 96/14334 A1 | 5/1996 |
| WO | 97/03635 A2 | 2/1997 |
| WO | 97/03681 A1 | 2/1997 |
| WO | 97/11174 A1 | 3/1997 |
| WO | 97/19065 A1 | 5/1997 |
| WO | 97/20842 A1 | 6/1997 |
| WO | 97/42222 A1 | 11/1997 |

(Continued)

OTHER PUBLICATIONS

Dupont e al. (Clin Immunol Immunopathol, 40(3), 1986, abstract only).*
Ball, Kathryn L. et al., "Cell-cycle arrest and inhibition of Cdk4 activity by small peptides based on the carboxy-terminal domain of p21WAF1," Current Biology, vol. 7:71-80 (1996).
Ball, Kathryn L. et al., "Human and plant proliferating-cell nuclear antigen have a highly conserved binding site for the p53-inducible gene product p21WAF1," Eur. J. Biochem., vol. 237:854-861 (1996).
Chen, I-Tsuen et al., "Characterization of p21Cip1/Waf1 peptide domains required for cyclin E/Cdk2 and PCNA interaction," Oncogene, vol. 12:595-607 (1996).
Chen, Junjie et al., "Cyclin-Binding Motifs Are Essential for the Function of p21CIP1," Molecular and Cellular Biology, vol. 16(9):4673-4682 (1996).

(Continued)

*Primary Examiner* — Bong-Sook Baek
(74) *Attorney, Agent, or Firm* — Nelson Mullins Riley & Scarborough LLP; Jane E. Remillard, Esq.; Cynthia L. Kanik

(57) ABSTRACT

The present invention relates to the use of an inhibitor of CDK2 and/or CDK7 and/or CDK9, or a pharmaceutically acceptable salt thereof, in the preparation of a medicament for treating a disease associated with antinuclear antibodies, wherein the inhibitor of CDK2 and/or CDK7 and/or CDK9 or pharmaceutically acceptable salt thereof is administered in an amount sufficient to down-regulate the levels of antinuclear antibodies. A further aspect of the invention relates to a combination comprising an inhibitor of CDK2 and/or CDK7 and/or CDK9, or a pharmaceutically acceptable salt thereof, and methylprednisolone, and its use in the treatment of diseases associated with antinuclear antibodies, such as SLE.

9 Claims, 17 Drawing Sheets

(56) References Cited

FOREIGN PATENT DOCUMENTS

| WO | 98/05335 A1 | 2/1998 |
|---|---|---|
| WO | 00/12485 A1 | 3/2000 |
| WO | 01/72745 A1 | 10/2001 |
| WO | 03/029248 A1 | 4/2003 |
| WO | 2004/043467 A1 | 5/2004 |
| WO | 2004/043953 A1 | 5/2004 |
| WO | 2004/056368 A1 | 7/2004 |
| WO | 2005/047526 A2 | 5/2005 |

OTHER PUBLICATIONS

Chen, Junjie et al., "p21Cip1/Waf1 disrupts the recruitment of human Fen1 by proliferating-cell nuclear antigen into the DNA replication complex," Proc. Natl. Acad. Sci. USA, vol. 93:11597-11602 (1996).
Chen, Junjie et al., "Separate domains of p21 involved in the inhibition of Cdk kinase and PCNA," Nature, vol. 374:386-388 (1995).
De Azevedo, Walter et al., "Inhibition of cyclin-dependent kinases by purine analogues, Crystal structure of human cdk2 complexed with roscovitine," Eur. J. Biochem., vol. 243:518-526 (1997).
Deng, Chuxia et al., "Mice Lacking p21CIP1/WAF1 Undergo Normal Development, but Are Defective in G1 Checkpoint Control," Cell, vol. 82:675-684 (1995).
Eastham, James A. et al., "In Vivo Gene Therapy with p53 or p21 Adenovirus for Prostate Cancer," Cancer Research, vol. 55:5151-5155 (1995).
El-Deiry, Wafik S. et al., "WAF1, a Potential Mediator of p53 Tumor Suppression," Cell, vol. 75:817-825 (1993).
Fåhraeus, Robin et al., "Inhibition of pRb phosphorylation and cell-cycle progression by a 20-residue peptide derived from p16CDKN2/INK4A," Current Biology, vol. 6(1):84-91 (1996).
Flores-Rozas, Hernan et al., "Cdk-interacting protein 1 directly binds with proliferating cell nuclear antigen and inhibits DNA replication catalyzed by the DNA polymerase d holoenzyme," Proc. Natl. Acad. Sci. USA, vol. 91:8655-8659 (1994).
Goubin, Francoise et al., "Identification of binding domains on teh p21Cip1 cyclin-dependent kinase inhibitor," Oncogene, vol. 10:2281-2287 (1995).
Grant, S. et al., "Crystal structure-based design of cyclin dependent kinase inhibitors," Proceedings of the American Association for Cancer Research, vol. 39:176 (1998).
Gray, Nathanael et al., "ATP-site Directed Inhibitors of Cyclin-dependent Kinases," Current Medicinal Chemistry, vol. 6(9):859-875 (1999).
Gu, Yong et al., "Inhibition of CDK2 activity in vivo by an associated 20K regulatory subunit," Nature, vol. 366:707-710 (1993).
Guzi, Timothy, "CYC-202 Cyclacel," Current Opinion in Investigational Drugs, vol. 5(12):1311-1318 (2004).
Hannon, Gregory J. et al., "p15INK4B is a potential effector of TGF-b-induced cell cycle arrest," Nature, vol. 371:257-261 (1994).
Harper, J. Wade et al., "Inhibition of Cyclin-dependent Kinases by p21," Molecular Biology of the Cell, vol. 6:387-400 (1995).
Harper, J. Wade et al., "The p21 Cdk-Interacting Protein Cip1 Is a Potent Inhibitor of G1 Cyclin-Dependent Kinases," Cell, vol. 75:805-816 (1993).
Havlicek, Libor et al., "Cytokinin-Derived Cyclin-Dependent Kinase Inhibitors: Synthesis and cdc2 Inhibitory Activity of Olomoucine and Related Compounds," J. Med. Chem., vol. 40:408-412 (1997).
Hiraoka, Lea R. et al., "Sequence of Human FEN-1, a Structure-Specific Endonuclease, and Chromosomal Localization of the Gene (FEN1) in Mouse and Human," Genomics, vol. 25:220-225 (1995).
Iseki, Hideaki et al., "A Novel Strategy for Inhibiting Growth of Human Pancreatic Cancer Cells by Blocking Cyclin-Dependent Kinase Activity," Journal of Gastrointestinal Surgery, vol. 2:36-43 (1998).
Iseki, H. et al., "A Novel Strategy to Inhibiting Growth of Human Pancreatic Cancer Cells by Blocking Cyclin-Dependent Kinase Activity," Gastroenterology, vol. 112(4 Suppl.) No. A1451 (1997).
Iseki, Hideaki et al., "Cyclin-dependent kinase inhibitors block proliferation of human gastric cancer cells," Surgery, vol. 122:187-195 (1997).

Kamb, Alexander et al., "A Cell Cycle Regulator Potentially Involved in Genesis of Many Tumor Types," Science, vol. 264:436-440 (1994).
Krucher, Nancy A. et al., "The Cyclin-Dependent Kinase (cdk) Inhibitors, Olomoucine and Roscovitine, Alter the Expression of a Molluscan Circadian Pacemaker, " Cellular and Molecular Neurobiology, vol. 17(5):495-507 (1997).
Legraverend, Michel et al., "Synthesis of C2 Alkynylated Purines, a New Family of Potent Inhibitors of Cyclin-Dependent Kinases," Bioorganic & Medicinal Chemistry Letters, vol. 8:793-798 (1998).
Lin, Jiayuh et al., "Analysis of Wild-Type and Mutant p21WAF-1 Gene Activities," Molecular and Cellular Biology, vol. 16(4):1786-1793 (1996).
Luo, Yan et al., "Cell-Cycle inhibition by independent CDK and PCNA binding domains in p21Cip1," Nature, vol. 375:159-161 (1995).
Maas Jr., James W. et al., "Apoptosis of Central and Peripheral Neurons Can Be Prevented with Cyclin-Dependent Kinase/Mitogen-Activated Protein Kinase Inhibitors," Journal of Neurochemistry, vol. 70:1401-1410 (1998).
Maclachlan, Timothy K. et al., "Cyclins, Cyclin-Dependent Kinases and Cdk Inhibitors: Implications in Cell Cycle Control and Cancer," Critical Reviews in Eukaryotic Gene Expression, vol. 5(2):127-156 (1995).
Maijer, Laurent et al., "Biochemical and cellular effects of roscovitine, a potent and selective inhibitor of the cyclin-dependent kinases cdc2, cdk2 and cdk5," Eur. J. Biochem., vol. 243:527-536 (1997).
Mgbonyebi, Ozuem P. et al., "Roscovitine Inhibits the Proliferative Activity of Immortal and Neoplastic Human Breast Epithelial Cells," Anticancer Research, vol. 18:751-756 (1998).
Nakanishi, Makoto et al., "Identification of the active region of the DNA synthesis inhibitory gene p21Sdi1/CIP1/WAF1," The EMBO Journal, vol. 14(3):555-563 (1995).
Nakanishi, Makoto et al., "The C-terminal Region of p21SDI1/WAF1/CIP1 Is Involved in Proliferating Cell Nuclear Antigen Binding But Does Not Appearl to Be Required for Growth Inhibition," The Journal of Biological Chemistry, vol. 270(29):17060-17063 (1995).
Okamoto, Aikou et al., "Mutations and altered expression of p16INK4 in human cancer," Proc. Natl. Acad. Sci. USA, vol. 91:11045-11049 (1994).
Paul, Rolf et al., "Preparation of Substituted N-Phenyl-4-aryl-2-pyrimidinamines as Mediator Release Inhibitors," J. Med. Chem., vol. 36:2716-2725 (1993).
Pippin, Jeffrey W. et al., "Direct in vivo Inhibition of the Nuclear Cell Cycle Cascade in Experimental Mesangial Proliferative Glomerulonephritis with Roscovitine, a Novel Cyclin-dependent Kinase Antagonist," J. Clin. Invest., vol. 100(10):2512-2520 (1997).
Planchais, Severine et al., "Roscovitine, a novel cyclin-dependent kinase inhibitor, characterizes restriction point and G2/M transition in tobacco BY-2 cell suspension," The Plant Journal, vol. 12(1):191-202 (1997).
Quelle, Dawn E. et al., "Cloning and characterization of murine p16INK4a and p15INK4b genes," Oncogene, vol. 11:635-645 (1995).
Rudolph, Bettina et al., "Activation of cyclin-dependent kinases by Myc mediates induction of cyclinA, but not apoptosis," The EMBO Journal, vol. 15(12):3065-3076 (1996).
Schutte, Bert et al., "The Effect of the Cyclin-Dependent Kinase Inhibitor Olomoucine on Cell Cycle Kinetics," Experimental Cell Research, vol. 236:4-15 (1997).
Serrano, Manuel et al., "A new regulatory motif in cell-cycle control causing specific inhibition of cyclin D/CDK4," Nature, vol. 366:704-707 (1993).
Su, Jin-Yuan et al., "Cloning and characterization of the *Xenopus* cyclin-dependent kinase inhibitor p27XIC1," Proc. Natl. Acad. Sci. USA, vol. 92:10187-10191 (1995).
Van Engeland, Manon et al., "Plasma Membrane Alterations and Cytoskeletal Changes in Apoptosis," Experimental Cell Research, vol. 235:421-430 (1997).
Vesely, Jaroslav et al., "Inhibition of cyclin-dependent kinases by purine analogues," Eur. J. Biochem., vol. 224:771-786 (1994).

(56) References Cited

OTHER PUBLICATIONS

Waga, Shou et al., "The p21 inhibitor of cyclin-dependent kinases controls DNA replication by interaction with PCNA," Nature, vol. 369:574-578 (1994).
Waldman, Todd et al., "p21 Is Necessary for the p53-mediated G1 Arrest in Human Cancer Cells1," Cancer Research, vol. 55:5187-5190 (1995).
Warbrick, Emma et al., "A small peptide inhibitor of DNA replication defines the site of interaction between the cyclin-dependent kinase inhibitor p21WAF1 and proliferating cell nuclear antigen," Current Biology, vol. 5:275-282 (1995).
Warbrick, Emma et al., "Homologous regions of Fen1 and p21Cip1 compete for binding to the same site on PCNA: a potential mechanism to co-ordinate DNA replication and repair," Oncogene, vol. 14:2313-2321 (1997).
Xiong, Yue et al., "p21 is a universal inhibitor of cyclin kinases," Nature, vol. 366:701-704 (1993).
Yakisich, J. Sebastian et al., "Early Inhibition of DNA Synthesis in the Developing Rat Cerebral Cortex by the Purine Analogues Olomoucine and Roscovitine," Biochemical and Biophysical Research Communications, vol. 243:674-677 (1998).
Zhang, Hui et al., "p21-containing cyclin kinases exist in both active and inactive states," Genes & Development, vol. 8:1750-1758 (1994).
Zimmermann, Jürg et al., "Phenylamino-Pyrimidine (PAP)—Derivatives: A New Class of Potent and Highly Selective PDGF-Receptor Autophosphorylation Inhibitors," Bioorganic & Medicinal Chemistry Letters, vol. 6(11):1221-1226 (1996).
International Search Report for Application No. PCT/GB2005/003350, dated Feb. 27, 2006.

* cited by examiner

PURINE AND PYRIMIDINE CDK INHIBITORS AND THEIR USE FOR THE TREATMENT OF AUTOIMMUNE DISEASES

RELATED APPLICATIONS

This application is a continuation of U.S. Ser. No. 11/660,249, filed on Sep. 6, 2007 (abandoned), which is a 35 U.S.C. §371 national stage filing of PCT Application No. PCT/GB2005/003350 filed on Aug. 25, 2005, which claims priority to, and the benefit of, GB Application No. 0419175.5 filed on Aug. 27, 2004 and GB Application No. 0419176.3 filed on Aug. 27, 2004. The contents of the aforementioned applications are hereby incorporated by reference.

The present invention relates to a method of treating diseases associated with antinuclear antibodies. More specifically, but not exclusively, the invention relates to methods of treating autoimmune rheumatic diseases such as human systemic lupus erythematosus (SLE), and pharmaceutical compositions and combinations therefor.

BACKGROUND TO THE INVENTION

The purpose of the immune system is to protect the body from potentially harmful substances (antigens) such as microorganisms, toxins, cancer cells, and foreign blood or tissues from another person or species. Antigens are destroyed by the immune response, which includes production of antibodies (molecules that attach to the antigen and make it more susceptible to destruction) and sensitized lymphocytes (specialized white blood cells that recognize and destroy particular antigens).

Immune system disorders occur when the immune response is inappropriate, excessive, or lacking. Autoimmune disorders refers to any disease characterized by abnormal functioning of the immune system that causes the immune system to produce antibodies against its own tissues. This is caused by a hypersensitivity reaction where the immune system reacts to substances that it normally would ignore, i.e. normal "self" body tissues.

Normally, the immune system is capable of differentiating "self" from "non-self" tissue. Some immune system cells (lymphocytes) become sensitized against "self" tissue cells, but these faulty lymphocytes are usually controlled (suppressed) by other lymphocytes. Autoimmune disorders occur when the normal control process is disrupted, or if normal body tissue is altered so that it is no longer recognized as "self."

Autoimmune disorders typically result in destruction of one or more types of body tissues, abnormal growth of an organ, or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or pancreas, organs such as the kidney or liver, muscles, joints, and skin.

Examples of autoimmune or autoimmune-related disorders include: Hashimoto's thyroiditis, pernicious anemia, Addison's disease, type I diabetes, rheumatoid arthritis, systemic lupus erythematosus, dermatomyositis, Sjogren's syndrome, drug-induced lupus erythematosus, multiple scleroris, myasthenia gravis, Reiter's syndrome and Grave's disease.

Symptoms of autoimmune diseases vary widely depending on the type of disease. However, autoimmune diseases are often associated with non-specific symptoms such as fatigue, dizziness, malaise (non-specific feeling of not being well), fever, and low-grade temperature elevations.

Specific autoimmune disease results in the destruction of an organ or tissue resulting in decreased functioning of an organ or tissue (for example, the islet cells of the pancreas are destroyed in diabetes), and/or an increase in size of an organ or tissue (for example, thyroid enlargement in Grave's disease). Symptoms vary depending on the specific disorder and the organ or tissue affected.

Autoimmunity is controlled through balanced suppression of the immune system. The aim is to reduce the immune response against normal body tissue whilst leaving intact the immune response against micro-organisms and abnormal tissues. Clinical treatments for autoimmune diseases typically involve the use of corticosteroids and immunosuppressants (including cyclophosphamide or azathioprine) which reduce the immune response. However, many of treatments available to date are associated with severe adverse side effects.

The present invention seeks to provide alternative therapeutic methods for treating autoimmune diseases which ideally are capable of reducing symptoms and controlling the autoimmune process, whilst maintaining the ability to fight disease. More particularly, the invention relates to the treatment of diseases associated with antinuclear antibodies, especially autoimmune diseases such as human systemic lupus erythematosus. The invention also seeks to provide pharmaceutical combinations and compositions suitable for treating such disorders.

STATEMENT OF INVENTION

A first aspect of the invention relates to the use of an inhibitor of CDK2 and/or CDK7 and/or CDK9, or a pharmaceutically acceptable salt thereof, in the preparation of a medicament for treating a disease associated with antinuclear antibodies, wherein the inhibitor of CDK2 and/or CDK7 and/or CDK9, or pharmaceutically acceptable salt thereof is administered in an amount sufficient to down-regulate the levels of antinuclear antibodies.

A second aspect of the invention relates to a method of treating a disease associated with antinuclear antibodies in a subject, said method comprising administering to the subject an inhibitor of CDK2 and/or CDK7 and/or CDK9, or a pharmaceutically acceptable salt thereof, in an amount sufficient to down-regulate the level of antinuclear antibodies.

A third aspect of the invention relates to a method of treating a disease associated with antinuclear antibodies in a subject by down-regulating the level of antinuclear antibodies in said subject, said method comprising administering an inhibitor of CDK2 and/or CDK7 and/or CDK9, or a pharmaceutically acceptable salt thereof, in an amount sufficient to down-regulate the level of antinuclear antibodies.

A fourth aspect of the invention relates to a method of treating a disease associated with antinuclear antibodies in a subject by down-regulating the level of antinuclear antibodies, said method comprising administering an inhibitor of CDK2 and/or CDK7 and/or CDK9, or a pharmaceutically acceptable salt thereof, such that said disease is treated.

A fifth aspect of the invention relates to a method of down-regulating the level of antinuclear antibodies in a subject, said method comprising administering an inhibitor of CDK2 and/or CDK7 and/or CDK9, or a pharmaceutically acceptable salt thereof, to said subject in an amount sufficient to down-regulate the level of antinuclear antibodies.

A sixth aspect of the invention relates to a method of down-regulating the level of antinuclear antibodies in a cell, said method comprising contacting said cell with an inhibitor of CDK2 and/or CDK7 and/or CDK9, or a pharmaceutically acceptable salt thereof, in an amount sufficient to down-regulate the level of antinuclear antibodies in said cell.

A seventh aspect of the invention relates to a pharmaceutical composition for treating a disease associated with antinuclear antibodies, said composition comprising an inhibitor of CDK2 and/or CDK7 and/or CDK9, in an amount sufficient to down-regulate the level of antinuclear antibodies, admixed with a pharmaceutically acceptable diluent, excipient or carrier.

An eighth aspect of the invention relates to a combination comprising an inhibitor of CDK2 and/or CDK7 and/or CDK9, or a pharmaceutically acceptable salt thereof, and methylprednisolone.

A ninth aspect relates to a pharmaceutical composition comprising a combination according to the invention and a pharmaceutically acceptable carrier, diluent or excipient.

A tenth aspect of the invention relates to a pharmaceutical product comprising an inhibitor of CDK2 and/or CDK7 and/or CDK9, or a pharmaceutically acceptable salt thereof, and methylprednisolone as a combined preparation for simultaneous, sequential or separate use in therapy.

An eleventh aspect of the invention relates to a pharmaceutical composition comprising:
an inhibitor of CDK2 and/or CDK7 and/or CDK9, or a pharmaceutically acceptable salt thereof; and
methylprednisolone;
admixed with a pharmaceutically acceptable diluent, excipient or carrier.

A twelfth aspect relates to a combination according to the invention in the preparation of a medicament for treating a disease associated with antinuclear antibodies.

A thirteenth aspect of the invention relates to the use of an inhibitor of CDK2 and/or CDK7 and/or CDK9, or a pharmaceutically acceptable salt thereof, in the preparation of a medicament for treating a disease associated with antinuclear antibodies, wherein the medicament is for use in combination with methylprednisolone.

A fourteenth aspect of the invention relates to the use of methylprednisolone in the preparation of a medicament for treating a disease associated with antinuclear antibodies, wherein the medicament is for use in combination with an inhibitor of CDK2 and/or CDK7 and/or CDK9, or a pharmaceutically acceptable salt thereof.

A fifteenth aspect of the invention relates to the use of an inhibitor of CDK2 and/or CDK7 and/or CDK9, or a pharmaceutically acceptable salt thereof, and methylprednisolone, in the preparation of a medicament for treating a disease associated with antinuclear antibodies.

A sixteenth aspect of the invention relates to the use of an inhibitor of CDK2 and/or CDK7 and/or CDK9, or a pharmaceutically acceptable salt thereof, in the preparation of a medicament for the treatment of a disease associated with antinuclear antibodies, wherein said treatment comprises administering to a subject simultaneously, sequentially or separately an inhibitor of CDK2 and/or CDK7 and/or CDK9, or a pharmaceutically acceptable salt thereof, and methylprednisolone.

A seventeenth aspect of the invention relates to a method of treating a disease associated with antinuclear antibodies in a subject, said method comprising administering to the subject a therapeutically acceptable amount of:
an inhibitor of CDK2 and/or CDK7 and/or CDK9, or a pharmaceutically acceptable salt thereof; and
methylprednisolone.

For ease of reference, these and further aspects of the present invention are now discussed under appropriate section headings. However, the teachings under each section are not necessarily limited to each particular section.

DETAILED DESCRIPTION

Inhibitors of CDK2 and/or CDK7 and/or CDK9

The present invention relates to the use of one or more inhibitors of CDK2 and/or CDK7 and/or CDK9. For the avoidance of doubt, the inhibitor may be an inhibitor of any one of CDK2, CDK7 or CDK9, or any combination thereof.

In one preferred embodiment, the inhibitor is an inhibitor of CDK2.

In another preferred embodiment, the inhibitor is an inhibitor of CDK7.

In another preferred embodiment, the inhibitor is an inhibitor of CDK9.

In another preferred embodiment, the inhibitor is an inhibitor of CDK7 and CDK9.

Methods for assaying CDK activity will be familiar to the skilled artisan. Further details are outlined in the accompanying Examples section.

Preferably, the inhibitor exhibits an $IC_{50}$ value for one or more of CDK2, CDK7 or CDK9 of less than 1 mM, more preferably less than 100 µM, more preferably still, less than 50 µM, more preferably less than 25 µM, more preferably less than 10 µM, even more preferably less than 1 µM or 0.5 or 0.1 µM.

Suitable examples of inhibitors of CDK2 and/or CDK7 and/or CDK9 include purine derivatives, such as those disclosed in EP 0874847B (CNRS), WO 03/002565 (Cyclacel Limited), WO 04/016613 (Cyclacel Limited) and WO 04/016612 (Cyclacel Limited); and pyrimidine derivatives such as those disclosed in WO01/72745, WO 02/079193, WO 03/029248, WO04/043953 (all in the name of Cyclacel Limited).

In one preferred embodiment of the invention, the inhibitor of CDK2 and/or CDK7 and/or CDK9 is selected from the following:

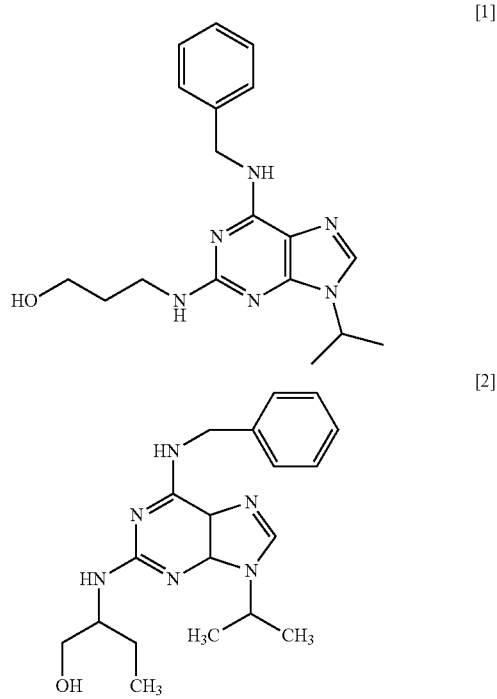

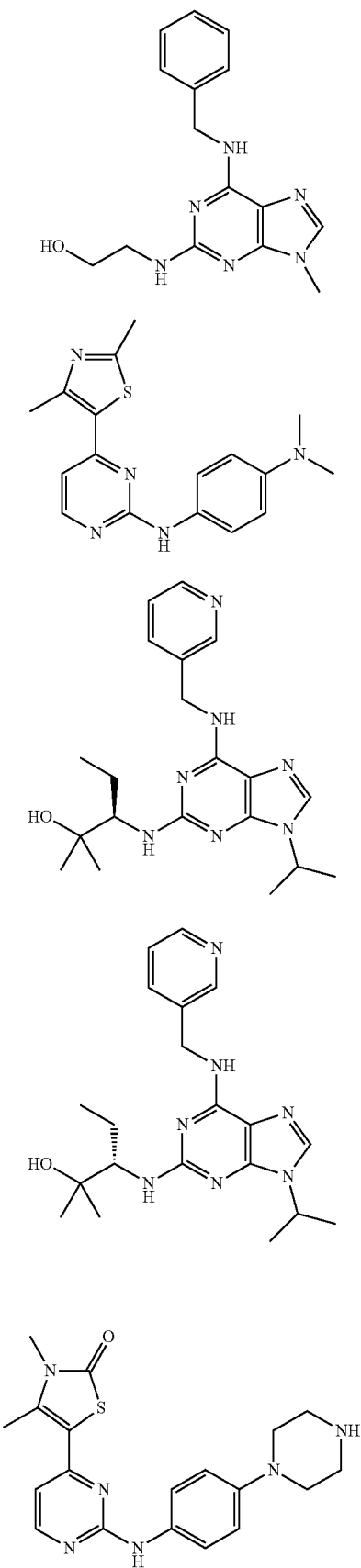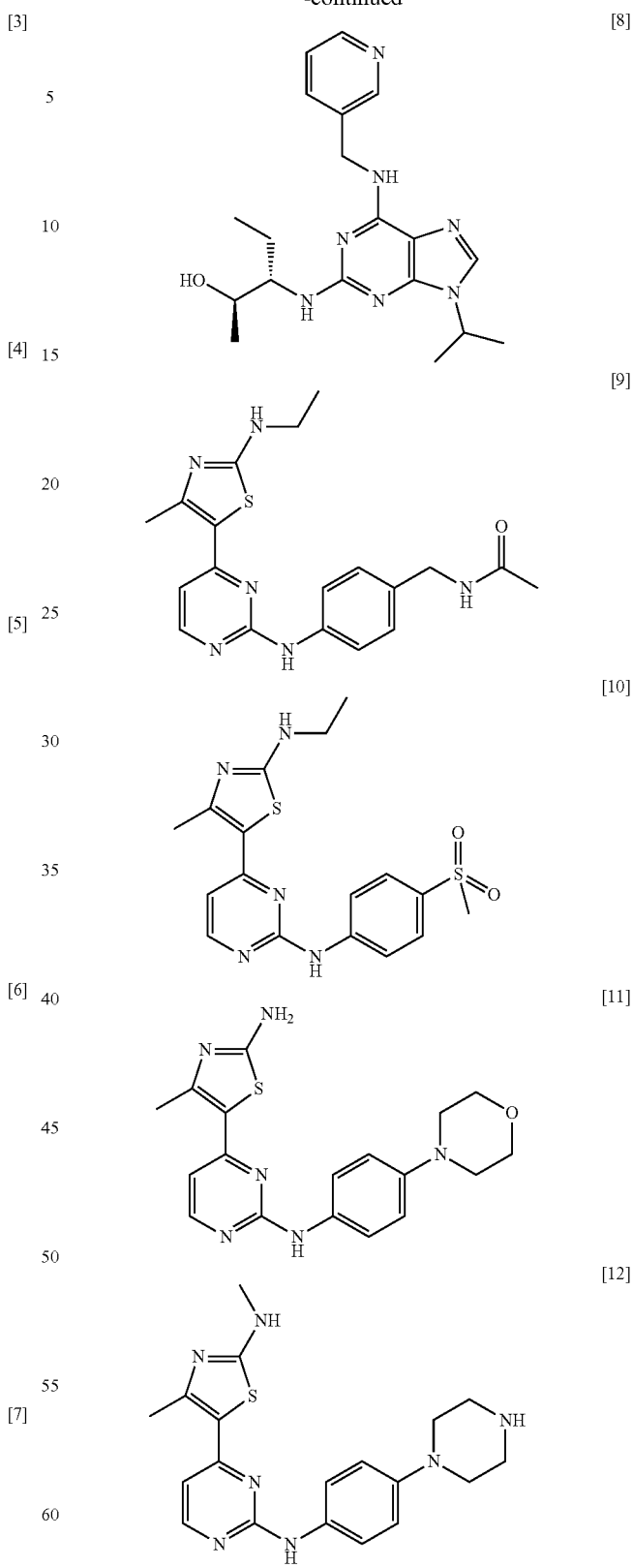
and pharmaceutically acceptable salts thereof.
In one particularly preferred embodiment, the inhibitor of CDK2 and/or CDK7 and/or CDK9 is selected from compounds [1]-[3], [5]-[8], [11] and [12].

In another particularly preferred embodiment, the inhibitor of CDK2 and/or CDK7 and/or CDK9 is selected from compounds [4], [9] and [10].

In yet another particularly preferred embodiment, the inhibitor of CDK2 and/or CDK7 and/or CDK9 is compound [7].

To date, there has been no suggestion that inhibitors of CDK2 and/or CDK7 and/or CDK9 would be effective in reducing the level of antinuclear antibodies. Nor has there been any teaching or suggestion in the art that such inhibitors could be used in combination therapy with methylprednisolone in the treatment of autoimmune disorders.

In one preferred embodiment, the inhibitor of CDK2 and/or CDK7 and/or CDK9 is selected from roscovitine, olomoucine and purvalanol A.

In an even more preferred embodiment of the invention, the inhibitor of CDK2 and/or CDK7 and/or CDK9 is roscovitine.

Roscovitine or 2-[(1-ethyl-2-hydroxyethyl)amino]-6-benzylamine-9-isopropylpurine, is also described as 2-(1-D,L-hydroxymethylpropylamino)-6-benzylamine-9-isopropylpurine. As used herein, the term "roscovitine" encompasses the resolved R and S enantiomers, mixtures thereof, and the racemate thereof.

As used herein, the term "CYC202" refers to the R enantiomer of roscovitine, namely, 2-(1-R-hydroxymethylpropylamino)-6-benzylamino-9-isopropylpurine, the structure of which is shown below.

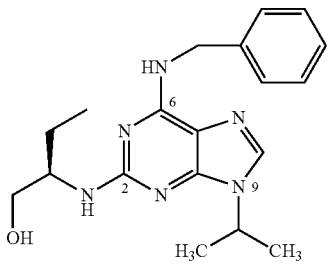 [SMILES: CC[C@H](CO)Nc1nc(NCc2ccccc2)c2ncn(C(C)C)c2n1]

The in vitro activity of roscovitine is as follows:

| Kinase | IC$_{50}$ (μM) |
|---|---|
| Cdk1/cyclin B | 2.7 |
| Cdk2/cyclin A | 0.7 |
| Cdk2/cyclin E | 0.1 |
| Cdk7/cyclin H | 0.5 |
| Cdk9/cyclin T1 | 0.8 |
| Cdk4/cyclin D1 | 14.2 |
| ERK-2 | 1.2 |
| PKA | >50 |
| PKC | >50 |

Although the use of roscovitine in the treatment of autoimmune disorders is documented in the art, to date, there has been no suggestion that it would be effective in reducing the level of antinuclear antibodies. Nor has there been any teaching or suggestion in the art that roscovitine could be used in combination therapy with methylprednisolone in the treatment of autoimmune disorders.

For all embodiments of the invention, preferably the roscovitine is in the form of the R enantiomer, namely 2-(1-R-hydroxymethylpropylamino)-6-benzylamino-9-isopropylpurine, hereinafter referred to as "CYC202".

Therapeutic Activity

As mentioned above, the present invention relates to the use of an inhibitor of CDK2 and/or CDK7 and/or CDK9, or a pharmaceutically acceptable salt thereof, in the preparation of a medicament for treating a disease associated with antinuclear antibodies, wherein the inhibitor of CDK2 and/or CDK7 and/or CDK9, or pharmaceutically acceptable salt thereof, is administered in an amount sufficient to down-regulate the levels of antinuclear antibodies.

Antinuclear antibodies (ANAs) are unusual antibodies, detectable in the blood, that have the capability of binding to certain structures within the nucleus of the cells. ANAs are found in patients whose immune system may be predisposed to cause inflammation against their own body tissues. Antibodies that are directed against one's own tissues are referred to as auto-antibodies. The propensity for the immune system to work against its own body is referred to as autoimmunity.

The presence of antinuclear antibodies is a hallmark of autoimmune diseases. Antinuclear antibodies are a diverse group of antibodies, often directed to large cellular complexes containing protein and nucleic acid components. The most frequently occurring antinuclear antibodies react with components of DNA-protein or RNA-protein complexes [Van Venrooij W. J. et al; Von Mulen C. A. et al]. Studies have indicated that the production of these autoantibodies, which are generally high-titre, high affinity IgG antibodies is T-cell dependent and driven by the host autoantigen [Reichlin M. et al].

For a disease to be defined as autoimmune, the tissue damage must be shown to be caused by an adaptive immune response to self antigens. Autoimmune diseases can be mediated by autoantibodies and/or by auto-reactive T cells, and tissue damage can result from direct attack on the cells bearing the antigen, from immune-complex formation, or from local inflammation. T cells can be involved directly in inflammation or cellular destruction, and they are also required to sustain autoantibody responses. Similarly, B cells may be important antigen-presenting cells for sustaining autoantigen-specific T-cell responses.

CD4 T cells selectively activate those B cells that bind epitopes that are physically linked to the peptide recognized by the T cell. Thus, both autoreactive B cells and autoreactive T cells are required for a disease involving autoimmunity.

Anti-nuclear antibody production can only be studied in vivo since the production of these antibodies requires a dysfunctional immune system comprising both B and T cells, and a failure to select and destroy immune cells that recognise self.

In vitro assays for T cell function are appropriate screening tools to identify compounds that may have the ability to modulate the immune response in the complex situation of autoimmune disease. One such assay is a T cell proliferation assay, further details of which are set forth in the accompanying Examples. In autoimmune diseases involving antinuclear antibody production normal T cell function is required to stimulate autoantibody production by B cells. Accordingly, compounds affecting T cell function (one measure of T cell function is the ability to proliferate in response to an immune stimulus) should also prevent the formation of autoantibodies, by controlling the ability of T cells to communicate with B cells and in addition by preventing T cells from migrating to the site of auto-immune damage.

As used herein, the term "antinuclear antibodies" includes both anti-DNA antibodies, anti-RNA antibodies and antibodies directed against protein nuclear components.

Diseases associated with antinuclear antibodies include autoimmune rheumatic diseases and organ specific autoimmunity.

Preferably, the autoimmune rheumatic disease is selected from drug induced lupus, systemic lupus erythematosis (SLE), and rheumatoid arthritis.

Rheumatoid arthritis is a chronic autoimmune disease that involves inflammation in the lining of the joints and/or other internal organs. Rheumatoid arthritis is a systemic disease that affects the entire body and is one of the most common forms of arthritis. It is characterized by the inflammation of the membrane lining the joint, which causes pain, stiffness, warmth, redness and swelling. The inflamed joint lining, the synovium, can invade and damage bone and cartilage. Inflammatory cells release enzymes that may digest bone and cartilage. The involved joint can lose its shape and alignment, resulting in pain and loss of movement. Symptoms typically include inflammation of joints, swelling, difficulty moving and pain. Other symptoms include loss of appetite, fever, loss of energy and anemia.

To date, treatment methods focus on relieving pain, reducing inflammation, stopping or slowing joint damage, and improving patient function and well-being. Medications can be divided into two groups: (i) symptomatic medications, (such as NSAIDS, aspirin, analgesics and corticosteroids) which help reduce joint pain, stiffness and swelling; and (ii) disease-modifying antirheumatic drugs, such as low doses of methotrexate, leflunomide, D-Penicillamine, sulfasalazine, gold therapy, minocycline, azathioprine, hydroxychloroquine (and other antimalarials), cyclosporine and biologic agents.

More preferably, the autoimmune rheumatic disease is systemic lupus erythematosis (SLE).

Systemic Lupus Erythematosus

In one preferred embodiment, the invention relates to the treatment of systemic lupus erythematosus (also known as disseminated lupus erythematosus; SLE; lupus; lupus erythematosus) is a chronic, inflammatory autoimmune disorder that may affect many organ systems including the skin, joints and internal organs. Although people with the disease may have many different symptoms, some of the most common ones include extreme fatigue, painful or swollen joints (arthritis), unexplained fever, skin rashes, and kidney problems. At present there is no cure for SLE.

The disease affects nine times as many women as men and appears more common in people of African descent. It may occur at any age, but appears most often in people between the ages of 10 and 50 years. SLE may also be caused by certain drugs. When this occurs, it is known as drug-induced lupus erythematosus and it is usually reversible when the medication is stopped.

The course of the disease may vary from a mild episodic illness to a severe fatal disease. Symptoms also vary widely in a particular individual over time and are characterized by periods of remission and exacerbation. Some of the most common symptoms of lupus include painful or swollen joints (arthritis), unexplained fever, and extreme fatigue. Other symptoms of lupus include chest pain, hair loss, anemia (a decrease in red blood cells), mouth ulcers, and pale or purple fingers and toes from cold and stress. Some people also experience headaches, dizziness, depression, confusion, or seizures. New symptoms may continue to appear years after the initial diagnosis, and different symptoms can occur at different times. At its onset, only one organ system may be involved. Additional organs may become involved later.

Lupus is characterized by periods of illness, called flares, and periods of wellness, or remission. Typically, once SLE has been diagnosed, the doctor will develop a treatment plan based on the patient's age, sex, health, symptoms, and lifestyle. In developing a treatment plan, the doctor has several goals: to prevent flares, to treat them when they do occur, and to minimize organ damage and complications.

To date, a number of different treatments are available for SLE sufferers. For people with joint or chest pain or fever, drugs that decrease inflammation, called nonsteroidal anti-inflammatory drugs (NSAIDs), are often used. Common side effects of NSAIDs can include stomach upset, heartburn, diarrhea, and fluid retention. Some sufferers also develop liver, kidney, or even neurological complications.

Antimalarials are another type of drug commonly used to treat lupus. Although they are generally used to treat fatigue, joint pain, skin rashes, and inflammation of the lungs, clinical studies have found that continuous treatment with antimalarials may prevent flares from recurring. Side effects of antimalarials can include stomach upset and, extremely rarely, damage to the retina of the eye.

The mainstay of lupus treatment involves the use of corticosteroid hormones. Corticosteroids work by rapidly suppressing inflammation and can be given by mouth, in creams applied to the skin, or by injection. Short-term side effects of corticosteroids include swelling, increased appetite, and weight gain. These side effects generally stop when the drug is stopped. However, it can often be dangerous to stop taking corticosteroids suddenly, so there is a need to wean the patient off them over an extended period of time. Long-term side effects of corticosteroids can include stretch marks on the skin, weakened or damaged bones (osteoporosis and osteonecrosis), high blood pressure, damage to the arteries, high blood sugar (diabetes), infections, and cataracts. Typically, the higher the dose and the longer they are taken, the greater the risk and severity of side effects.

For patients whose kidneys or central nervous systems are affected by lupus, immunosuppressives may be used. Immunosuppressives restrain the overactive immune system by blocking the production of immune cells. Side effects may include nausea, vomiting, hair loss, bladder problems, decreased fertility, and increased risk of cancer and infection. The risk for side effects increases with the length of treatment. As with other treatments for lupus, there is a risk of relapse after the immunosuppressives have been stopped.

The present invention provides alternative therapeutic treatments for SLE and other autoimmune rheumatic diseases. In particular, the invention aims to provide alternative treatments to immunosuppressants and steroids, which at least in the acute phase of the disease have excellent therapeutic effects but which lack major long term side effects.

In Vivo Studies

Studies were undertake to investigate the efficacy of CYC202 and combinations of CYC202/methylprednisolone in mice.

NZB/W F1 hybrid mice spontaneously develop a severe autoimmune disease reminiscent of human systemic lupus erythematosus. The disease manifests with early antinuclear antibody formation, development of an immune complex glomerulonephritis with proteinuria and progression to renal insufficiency with time, that also causes premature mortality in these mice. It is a disease of T and B cell dysfunction with the formation of autoantibodies against nuclear and endogenous antigens, among which nucleosomes, DNA complexed to histones, seem to be the most prominent.

In vivo, nucleosomes are generated by apoptosis, a process that appears disturbed in lupus. In conditions of insufficient removal of apoptotic cells, nucleosomes act as autoantigens to drive a T cell-dependent immune response, whose critical components are nucleosome-specific antibodies and nucleosome/IgG complexes. These bind to intrinsic constituents of the glomerular basement membrane and promote inflammation. Cytokines and chemoattractants generated in exuberant amount by renal resident and infiltrating cells amplify and perpetuate immune complex-mediated injury.

Histologically, glomerular changes in NZB/W mice include endocapillary hypercellularity associated with focal extracapillary proliferation; immune-type deposits are detected in the mesangium and on subendothelial aspect of the glomerular basement membrane (GBM). Tubular damage, interstitial inflammation and fibrosis are severe.

There is increasing evidence showing that positive (cyclins and cyclin-dependent kinases) and negative (cyclin-dependent kinase inhibitors) cell cycle regulatory proteins have a critical role in regulating cellular responses to immune and nonimmune forms of injury, including cell proliferation and apoptosis. Proliferation of intrinsic glomerular cells such as mesangial cells is a characteristic response to forms of immune-mediated glomerular injury such as IgA nephropathy, lupus, and membranoproliferative glomerulonephritis. The expression of positive cell cycle proteins (cyclins D, E, A) as well as CDK2 protein levels and activity are increased in experimental mesangioproliferative glomerulonephritis (Thy nephritis) characterized by mesangial cell proliferation. In this model, inhibiting CDK2 decreased mesangial cell proliferation and matrix protein accumulation and improved renal function.

In vivo studies by the applicant have shown that NZB/W F1 mice treated with CYC202 at the doses of 200 and 100 mg/kg, starting from 2 months of age, survived significantly (P<0.05) longer than vehicle-treated mice. At the end of the study (month 8) while only four of thirteen NZB/W mice (31%) that had been treated with vehicle were alive, ten of thirteen mice (77%) and ten of fourteen mice (71%) treated with 200 and 100 mg/kg CYC202, respectively, survived. In the group of mice given CYC202 (100 mg/kg) from 5 months of age (therapeutic treatment) the percentage of survival was not different from that recorded in vehicle-treated mice.

In one preferred embodiment of the invention the amount of the inhibitor of CDK2 and/or CDK7 and/or CDK9 is sufficient to delay the onset of proteinuria and renal function impairment.

Cumulative percentage of mice with heavy proteinuria (>4 mg/day) was evaluated at different stages of the disease in all of the experimental groups. In the vehicle group the percentage of mice with proteinuria progressively increased over time. At the end of the study the percentage of proteinuric mice was 85%. CYC202 given as a preventive therapy from 2 months of age significantly delayed the onset of proteinuria compared to vehicle, in a dose-dependent manner (% proteinuric mice, month 8: 200 mg/kg, 23%, P<0.01 vs vehicle; 100 mg/kg, 43%, P<0.05 vs vehicle). When CYC202 was administered to lupus mice from 5 months of age a tendency toward a reduced percentage of proteinuric mice in respect to vehicle was observed, which however did not reach the statistical significance.

Renal function, assessed by serum blood urea nitrogen (BUN), was measured at 5 and 8 months. At 5 months serum BUN levels were within the normal range (<29 mg/dl) in all the experimental groups. In the vehicle group, renal function deteriorated with time and at 8 months 50% of the surviving animals had BUN levels ≥30 mg/dl. CYC202 given as preventive therapy from 2 months of age resulted in a better renal function of lupus mice, whereas it was not effective when administered at the later age of 5 months.

In one preferred embodiment of the invention, the amount of the inhibitor of CDK2 and/or CDK7 and/or CDK9 is sufficient to down-regulate the levels of anti-nuclear, specifically anti-DNA antibodies.

Elevated anti-DNA antibody levels are characteristic of NZB/W F1 mice. Mice given vehicle exhibited increasing levels of anti-DNA antibodies over time. Either at 5 or 8 months of age, mice treated from 2 months with CYC202 at both doses showed anti-DNA antibody levels significantly lower than vehicle. In the group of mice receiving CYC202 from 5 months anti-DNA antibody concentration was numerically, albeit not significantly lower than vehicle at 8 months.

In one preferred embodiment, the inhibitor of CDK2 and/or CDK7 and/or CDK9 is in an amount sufficient to reduce glomerular and tubointerstitial changes.

At the end of the study NZB/W mice given vehicle revealed glomerular changes with intracapillary hypercellularity associated with a focal extracapillary proliferation. Immune deposits were detected in the mesangium and on the subendothelial aspect of the glomerular basement membrane. Tubular damage and interstitial inflammation were also observed. Treatment from 2 months of age with CYC202 markedly limited glomerular hypercellularity, immune deposits, and tubulointerstitial damage. These effects were more pronounced when CYC202 was given at the dose of 200 mg/kg. Only a mild effect on renal morphology was observed in mice administered CYC202 from 5 months of age.

In one preferred embodiment, the amount of the inhibitor of CDK2 and/or CDK7 and/or CDK9 is sufficient to inhibit T-cell proliferation induced by PMA and ConA.

In one preferred embodiment of the invention, the inhibitor of CDK2 and/or CDK7 and/or CDK9 is in an amount sufficient to down-regulate the expression of Mcl-1.

In one preferred embodiment, the amount of the inhibitor of CDK2 and/or CDK7 and/or CDK9 is in an amount sufficient to reduce the interstitial accumulation of mononuclear cells.

Kidneys were analysed for F4/80 positive monocytes/macrophages by immunohistochemical technique. A marked accumulation of F4/80 positive cells was present in the renal interstitium of NZB/W mice given vehicle. Preventive treatment from 2 months of age with 200 mg/kg CYC202 remarkably reduced the number of F4/80 positive monocytes/macrophages in respect to vehicle. CYC202 at the dose of 100 mg/kg limited albeit not to a statistically significant degree the interstitial accumulation of mononuclear cells. A numerical reduction of F4/80 positive cells was observed in the therapeutic study (treatment from 5 months of age).

By way of summary, the results of the present study clearly indicate that CYC202 (200 and 100 mg/kg) given as a preventive therapy from 2 months of age, retarded renal manifestation of lupus in NZB/W mice and remarkably prolonged life as compared to animals given vehicle. Specifically, CYC202 delayed the onset of proteinuria and renal function impairment, and limited glomerular and tubulointerstitial changes including the interstitial accumulation of mononuclear cells, glomerular hypercellularity and immune deposits. The effects are more pronounced at the dose of 200 mg/kg. A remarkable finding of the present study was the reduction of the levels of anti-DNA antibodies by CYC202, which could possibly be attributed to CYC202 effects on T cells, which in turn may affect B cells. By in vitro experiments, a concentration-dependent inhibition of T cell proliferation induced by PMA and ConA, as well as in mixed lymphocyte reaction, has been observed following treatment with CYC202. Furthermore, there is evidence that in SLE, activated autoimmune T helper cells specific for histones or nucleosomes may provide help for B cells to differentiate into anti-DNA producing plasma cells (for review see Rekvig, Arthritis & Rheumatism 48: 300-312, 2003).

CYC202 is also known to have an effect on transcription, including downregulation of the anti-apoptotic protein mcl-1 and is thus capable of altering the balance of survival signals in cells. Anergic T cells may be specifically sensitive to this mechanism of action.

The administration of CYC202 (100 mg/kg) initiated at 5 months of age resulted in a mild reduction of the percentage of proteinuric mice and of renal damage in respect to vehicle-mice. Survival was not ameliorated. The modest effect was probably due to the low dose.

Combinations

In one particularly preferred embodiment, the medicament is for use in combination therapy with methylprodnisolone.

As used herein, the term "combination therapy" refers to therapy in which the methylprednisolone and the inhibitor of CDK2 and/or CDK7 and/or CDK9, are administered, if not simultaneously, then sequentially within a timeframe that they both are available to act therapeutically within the same time-frame.

Another aspect of the invention relates to a combination comprising an inhibitor of CDK2 and/or CDK7 and/or CDK9, or a pharmaceutically acceptable salt thereof, and methylprednisolone.

Preferably, the combination has a synergistic effect, i.e. the combination is synergistic. Methylprednisolone is a synthetic (man-made) corticosteroid. The chemical name is 11,17,21-trihydroxy-6-methyl-(6a,11b)-pregna-1,4-diene-3,20-dione Corticosteroids are naturally-occurring chemicals produced by the adrenal glands located adjacent to the kidneys. Corticosteroids block inflammation and are used in a wide variety of inflammatory diseases. There are numerous preparations of corticosteroids including oral tablets, capsules, liquids, topical creams and gels, inhalers, eye drops, and injectable and intravenous solutions. Methylprednisolone is typically prescribed as an oral tablet or liquid.

Methylprednisolone is used to achieve prompt suppression of inflammation. Examples of inflammatory conditions for which methylprednisolone is used include rheumatoid arthritis, systemic lupus erythmatosus, acute gouty arthritis, psoriatic arthritis, ulcerative colitis, and Crohn's disease. Severe allergic conditions that fail conventional treatment also may respond to methylprednisolone. Examples include bronchial asthma, allergic rhinitis, drug-induced dermatitis, and contact and atopic dermatitis. Chronic skin conditions treated with methylprednisolone include dermatitis herpetiformis, pemphigus, severe psoriasis and severe seborrheic dermatitis. Chronic allergic and inflammatory conditions of the uvea, iris, conjunctiva and optic nerves of the eyes also are treated with methylprednisolone.

Another aspect relates to a pharmaceutical composition comprising a combination according to the invention and a pharmaceutically acceptable carrier, diluent or excipient.

Another aspect of the invention relates to a pharmaceutical product comprising an inhibitor of CDK2 and/or CDK7 and/or CDK9, or a pharmaceutically acceptable salt thereof, and methylprednisolone as a combined preparation for simultaneous, sequential or separate use in therapy.

The inhibitor of CDK2 and/or CDK7 and/or CDK9 and methylprednisolone may be administered simultaneously, in combination, sequentially or separately (as part of a dosing regime).

As used herein, "simultaneously" is used to mean that the two agents are administered concurrently, whereas the term "in combination" is used to mean they are administered, if not simultaneously, then "sequentially" within a timeframe that they both are available to act therapeutically within the same time-frame. Thus, administration "sequentially" may permit one agent to be administered within 5 minutes, 10 minutes or a matter of hours after the other provided the circulatory half-life of the first administered agent is such that they are both concurrently present in therapeutically effective amounts. The time delay between administration of the components will vary depending on the exact nature of the components, the interaction therebetween, and their respective half-lives.

In contrast to "in combination" or "sequentially", "separately" is used herein to mean that the gap between administering one agent and the other is significant i.e. the first administered agent may no longer be present in the bloodstream in a therapeutically effective amount when the second agent is administered.

Yet another aspect of the invention relates to a pharmaceutical composition comprising:
(i) an inhibitor of CDK2 and/or CDK7 and/or CDK9, or a pharmaceutically acceptable salt thereof; and
(ii) methylprednisolone;
admixed with a pharmaceutically acceptable diluent, excipient or carrier.

A further aspect relates to a combination according to the invention in the preparation of a medicament for treating a disease associated with antinuclear antibodies.

A further aspect of the invention relates to the use of an inhibitor of CDK2 and/or CDK7 and/or CDK9, or a pharmaceutically acceptable salt thereof, in the preparation of a medicament for treating a disease associated with antinuclear antibodies, wherein the medicament is for use in combination with methylprednisolone.

Yet another aspect of the invention relates to the use of methylprednisolone in the preparation of a medicament for treating a disease associated with antinuclear antibodies, wherein the medicament is for use in combination with an inhibitor of CDK2 and/or CDK7 and/or CDK9, or a pharmaceutically acceptable salt thereof.

A further aspect of the invention relates to the use of an inhibitor of CDK2 and/or CDK7 and/or CDK9, or a pharmaceutically acceptable salt thereof, and methylprednisolone, in the preparation of a medicament for treating a disease associated with antinuclear antibodies.

Another aspect of the invention relates to the use of an inhibitor of CDK2 and/or CDK7 and/or CDK9, or a pharmaceutically acceptable salt thereof, in the preparation of a medicament for the treatment of a disease associated with antinuclear antibodies, wherein said treatment comprises administering to a subject simultaneously, sequentially or separately an inhibitor of CDK2 and/or CDK7 and/or CDK9, or a pharmaceutically acceptable salt thereof, and methylprednisolone.

A further aspect of the invention relates to a method of treating a disease associated with antinuclear antibodies in a subject, said method comprising administering to the subject a therapeutically acceptable amount of:
(i) an inhibitor of CDK2 and/or CDK7 and/or CDK9, or a pharmaceutically acceptable salt thereof; and
(ii) methylprednisolone.

For all of the above embodiments, preferably, the inhibitor of CDK2 and/or CDK7 and/or CDK9 and methylprednisolone are administered simultaneously or sequentially.

In one preferred embodiment, the inhibitor of CDK2 and/or CDK7 and/or CDK9 and methylprednisolone are administered simultaneously.

In one particularly preferred embodiment, the inhibitor of CDK2 and/or CDK7 and/or CDK9, is administered to the subject prior to sequentially or separately administering methylprednisolone to said subject.

Another aspect of the invention relates to a method of treating a proliferative disorder comprising the sequential administration of a therapeutically effective amount of an inhibitor of CDK2 and/or CDK7 and/or CDK9, followed by a therapeutically effective amount of methylprednisolone.

Another aspect of the invention relates to the use of an inhibitor of CDK2 and/or CDK7 and/or CDK9 in the manufacture of a medicament for use in the treatment of proliferative disorders comprising the sequential administration of a therapeutically effective amount of an inhibitor of CDK2 and/or CDK7 and/or CDK9, followed by a therapeutically effective amount of methylprednisolone.

In an alternative preferred embodiment, methylprednisolone is administered to the subject prior to sequentially or separately administering the inhibitor of CDK2 and/or CDK7 and/or CDK9 to said subject.

In one particularly preferred embodiment, the inhibitor of CDK2 and/or CDK7 and/or CDK9 and methylprednisolone are administered sequentially.

In one preferred embodiment of the invention, the inhibitor of CDK2 and/or CDK7 and/or CDK9 and methylprednisolone are each administered in a therapeutically effective amount with respect to the individual components.

In another preferred embodiment of the invention, the inhibitor of CDK2 and/or CDK7 and/or CDK9 and methylprednisolone are each administered in a subtherapeutic amount with respect to the individual components.

Preferably, the inhibitor of CDK2, CDK7 or CDK9 is as described above for the first aspect of the invention.

Pharmaceutical Compositions

As mentioned above, various aspects of the invention relate to pharmaceutical compositions.

Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients", $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds used in the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as $(C_1\text{-}C_4)$-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as $(C_1\text{-}C_4)$-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes the use of, where appropriate, all enantiomers and tautomers of the compounds involved. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

The compounds used in the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those agents, and mixtures thereof. The terms used in the claims encompass these forms, provided said forms retain the appropriate functional activity (though not necessarily to the same degree).

The present invention also includes the use of all suitable isotopic variations of the agent or pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes the use of solvate forms of the compounds of the present invention. The terms used in the claims encompass these forms.

Polymorphs

The invention furthermore relates to the use of compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the ues of compounds of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed Tablets, pills, Tablets, gellules, drops, and capsules. Preferably, these compositions contain from 1 mg to 5000 mg and more preferably from 10 mg-3000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-3000 mg, preferably between 10-1000 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 3500 mg/day will be administered to the patient.

The present invention is further illustrated by way of example, and with reference to the following Figures wherein.

EXAMPLES

Figure 1:
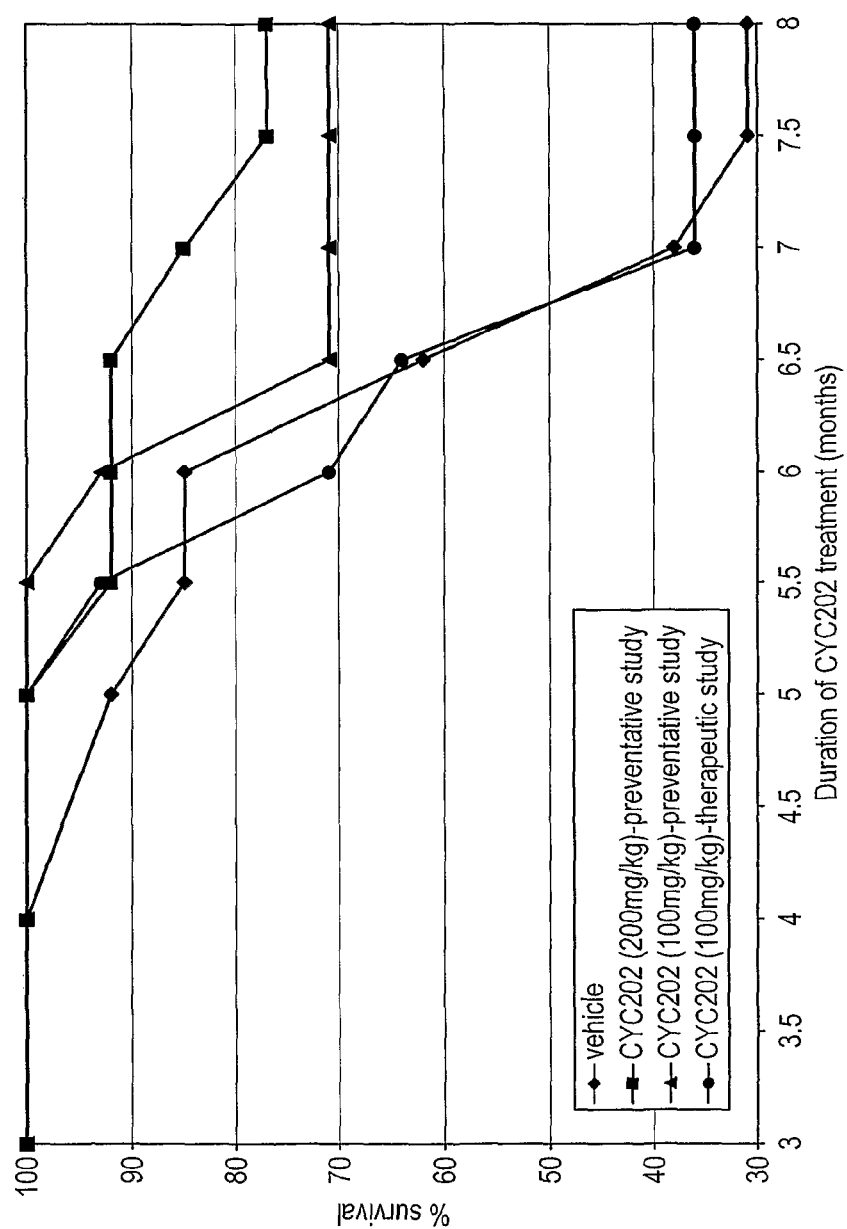
FIG. 1 shows the percentage survival against the duration of treatment (months) for NZB/W F1 mice treated with CYC202 at dosages of 100 and 200 mg/kg from 2 months or 5 months.

Inhibitors of CDK2 and/or CDK7 and/or CDK9

Various inhibitor compounds were prepared in accordance with the methods described in EP 0874847B (CNRS); and WO 03/002565, WO 04/016613, WO 04/016612, WO01/72745, WO 02/079193, WO 03/029248, WO04/043953 (all in the name of Cyclacel Limited).
Kinase Assays Kinase activity was investigated by measuring the incorporation of radioactive phosphate from ATP into appropriate polypeptide substrates. Recombinant protein kinases and kinase complexes were produced or obtained commercially. Assays were performed using 96-well plates and appropriate assay buffers (typically 25 mM β-glycerophosphate, 20 mM MOPS, 5 mM EGTA, 1 mM DTT, 1 mM $Na_3VO_3$, pH 7.4), into which were added 2-4 μg of active enzyme with appropriate substrates. The reactions were initiated by addition of Mg/ATP mix (15 mM $MgCl_2$+100 μM ATP with 30-50 kBq per well of [$\gamma$-$^{32}$P]-ATP) and mixtures incubated as required at 30° C. Reactions were stopped on ice, followed by filtration through p81 filterplates or GF/C filterplates (Whatman Polyfiltronics, Kent, UK). After washing 3 times with 75 mM aq orthophosphoric acid, plates were dried, scintillant added and incorporated radioactivity measured in a scintillation counter (TopCount, Packard Instruments, Pangbourne, Berks, UK). Compounds for kinase assay were made up as 10 mM stocks in DMSO and diluted into 10% DMSO in assay buffer. Data was analysed using curve-fitting software (GraphPad Prism version 3.00 for Windows, GraphPad Software, San Diego Calif. USA) to determine $IC_{50}$ values (concentration of test compound which inhibits kinase activity by 50%).
CDK 7 and 9 Assay CTD peptide substrate (biotinyl-Ahx-(Tyr-Ser-Pro-Thr-Ser-Pro-Ser)$_4$-NH$_2$; 1-2 mg/mL) and recombinant human CDK7/cyclin H, CDK9/cyclin T1, or CDK9/cyclin K (0.5-2 μg) were incubated for 45 min at 30° C. in the presence of varying amounts of test compound in 20 mM MOPS pH 7.2, 25 mM β-glycerophosphate, 5 mM EGTA, 1 mM DTT, 1 mM sodium vanadate, 15 mM $MgCl_2$, and 100 μM ATP (containing a trace amount of $^{32}$PγATP) in a total volume of 25 μL in a 96-well microtiter plate. The reaction was stopped by placing the plate on ice for 2 min. Avidin (50 μg) was added to each well, and the plate was incubated at room temp for 30 min. The samples were transferred to a 96-well P81 filter plate, and washed (4×200 μL per well) with 75 mM phosphoric acid. Microscint 40 scintillation liquid (50 μL) was added to each well, and the amount of $^{32}$P incorporation for each sample was measured using a Packard Topcount microplate scintillation counter.

CYC202

Studies were undertaken to evaluate whether administration of the CDK2 inhibitor CYC202 was effective in retarding the development of renal disease of NZB/WF1 lupus prone mice.

NZBxNZW F1 female mice (Harlan Italy s.r.l., Milano, Italy) of 2 months of age at the start of the experiment, were used Animal care and treatment were conducted in accordance with the institutional guidelines that are in compliance with national (Decreto Legislativo n. 116, Gazzetta Ufficiale suppl 40, 18 febbraio 1992, Circolare n. 8, Gazzetta Ufficiale 14 luglio 1994) and international laws and policies (EEC Council Directive 86/609, OJL358-1, December 1987; *Guide for the Care and Use of Laboratory Animals*, U.S. National Research Council, 1996). Animals were housed in a constant temperature room with a 12-hour dark/12-hour light cycle and were fed a standard diet.

Example 1

NZBxNZW F1 mice were randomly allocated to the following groups:
Group 1 (n=18): mice that were given daily by gavage the vehicle (HC150 mM);
Group 2 (n=17): mice that were given daily by gavage CYC202 (200 mg/kg);
Group 3 (n=19): mice that were given daily by gavage CYC202 (100 mg/kg);
Treatments started at 2 months of age (preventive study) and lasted until 8 months;
Four-five animals of each group were sacrificed at 5 months for evaluation of serum BUN and levels of circulating anti-DNA antibodies.

An additional group, Group 4 (n=14 mice) was given daily by gavage CYC202 (100 mg/kg) starting at 5 months of age, a time when immune complex deposition is actively taking place, until 8 months (therapeutic study). Five normal CD-1 mice (Charles River Italia, Calco, Italy) were used as control.

The following parameters were evaluated:
Urinary protein excretion: determined every month until 5 months of age and then every two weeks.
At sacrifice:
Anti-DNA antibodies in the serum;
Serum BUN;
Serum transaminase (AST, ALT);
Renal histology;
Accumulation of monocytes/macrophages into the renal interstitium.

Example 2

Lupus mice were randomly allocated to the following groups:
Group 1 (n=10): mice that were given daily by gavage the vehicle (HCl 50 mM);
Group 2 (n=15): mice that were given daily by gavage CYC202 at the dose of 200 mg/kg;
Group 3 (n=12): mice that were given daily by intraperitoneal injection methylprednisolone (MPS, Urbason, Hoechst s.p.a, Milano, Italy) at the dose of 1.5 mg/kg;
Group 4 (n=16): mice that were given daily CYC202 (200 mg/kg) in combination with MPS (1.5 mg/kg).

Treatments started at 5 months of age, a time when immunecomplex deposition is actively taking place and lasted until 12 months when the last animal receiving the vehicle treatment died. Five normal CD-1 mice (Charles River Italia, Calco, Italy) were used as control.

The following parameters were evaluated:

Survival;

Urinary protein excretion: determined every month until 5 months of age and then every two weeks;

Serum BUN: measured at month 5 (before treatment) and every month until the end of the study;

Renal histology: evaluated in biopsies from mice that were terminally ill and from mice survived until 12 months;

Accumulation of F4/80 positive monocytes/macrophages into the renal interstitium (evaluated in the same biopsies as above).

Examples 1 and 2

Materials And Methods

Proteinuria and Renal Function

Urinary protein concentration was determined by the Coomassie blue G dye-binding assay with bovine serum albumin as standard. Renal function was assessed as BUN in heparinized blood by the Reflotron test (Roche Diagnostics Corporation, Indianapolis, USA). BUN levels exceeding 30 mg/dl were considered abnormal (normal range in this laboratory for mice: 14-29 mg/dl).

Anti-DNA Antibodies

The levels of anti-dsDNA autoantibodies were evaluated in the serum by an enzyme-immunoassay (Diastat anti-ds DNA kit, Bouty Laboratory, Milano, Italy) as described before (Kidney Int, 53:726-734, 1998).

Serum Transaminase

Serum levels of AST and ALT were measured using an autoanalyzer (CX5, Beckman Instruments Inc., Fullerton, Calif.).

Renal Morphology

Light Microscopy:

Fragments of renal cortex were fixed in Dubosq-Brazil, dehydrated in alcohol and embedded in paraffin. Sections (3 µm) were stained with hematoxylin and eosin, Masson's trichrome, and periodic acid-Schiff's reagent (PAS-stain). Glomerular intracapillary hypercellularity was evaluated in a semiquantitative fashion by a scoring system from 0 to 3+(0=no hypercellularity; 1+=mild; 2+=moderate; 3+=severe). A single score was given for other changes based on the percentages of total glomeruli involved with a lesion. Extracapillary proliferation was graded from 0 to 3+(0=no hypercellularity; 1+=less than 25% of glomeruli involved; 2+=25% to 50% of glomeruli involved; 3+=more than 50% of glomeruli involved). Glomerular deposits were graded from 0 to 3+(0=no deposits; 1+=less than 25% of glomeruli involved; 2+=25% to 50% of glomeruli involved; 3+=more than 50% of glomeruli involved). Tubular (atrophy, casts and dilatation) and interstitial changes (fibrosis and inflammation) were graded from 0 to 3+(0=no changes; 1+=changes affecting less than 25% of the sample; 2+=changes affecting 25 to 50% of the sample; 3+=changes affecting more than 50% of the sample). At least 100 glomeruli were examined for each biopsy. At least 10 fields per sample were examined at low magnification (10×) for histologic scoring of the interstitium. All renal biopsies have been analyzed by the same pathologist, in a single-blind fashion.

Immunohistochemical Analysis

Rat monoclonal antibody against a cytoplasmic antigen present in mouse monocytes and macrophages (F4/80, 4 µg/ml, Caltag Laboratories, Burlingame, Calif.) was used for the detection of infiltrating cells by immunoperoxidase technique. Sections were incubated for 30 minutes with 0.3% $H_2O_2$ in methanol to quench endogenous peroxidase. Then the tissue was permeabilized in 0.1% Triton X-100 in PBS 0.01 mol/L, PH 7.2, for 30 minutes and then incubated with normal goat serum (Vector Laboratories) for 30 minutes. Primary antibody was incubated overnight at 4° C., followed by the secondary antibody (biotinylated goat anti-rat IgG, Vector Laboratories) and avidin-biotin peroxidase complex (ABC) solution, and finally development with DAB. The sections were counterstained with Harris hematoxylin. Negative controls were obtained by omitting the primary antibody. F40/80 labelled cells were counted in at least 10 randomly selected high power microscopic fields (×400) per each animal.

Statistical Analysis

Data are expressed as mean±Standard Error (SE). Survival curves were analyzed by log-rank test. Proteinuria data were analyzed by Fisher's exact test. All the other parameters were analyzed by Kruskall Wallis test. Statistical significance was defined as P<0.05.

Example 1

Results

Body Weight, Food and Water Intake

As shown in Table 1 lupus mice gained weight during the study. No difference in body weight was observed among the experimental groups. Food (Table 2) and water (Table 3) intake evaluated every two weeks from 2 to 5 months were comparable among vehicle and CYC202 treated mice.

Lupus Mice Survival

NZB/W F1 mice treated with CYC202 at the doses of 200 and 100 mg/kg, starting from 2 months of age, survived significantly (P<0.05) longer than vehicle-mice (see Table 4 and FIG. 1). Actually, at the end of the study (month 8) while only four of thirteen NZB/W mice (31%) that had been treated with vehicle were alive, ten of thirteen mice (77%) and ten of fourteen mice (71%) treated with 200 and 100 mg/kg CYC202, respectively, survived. In the group of mice given CYC202 (100 mg/kg) from 5 months of age (therapeutic treatment) the percentage of survival was not different from that recorded in vehicle-mice.

Proteinuria and Renal Function

Figure 2:
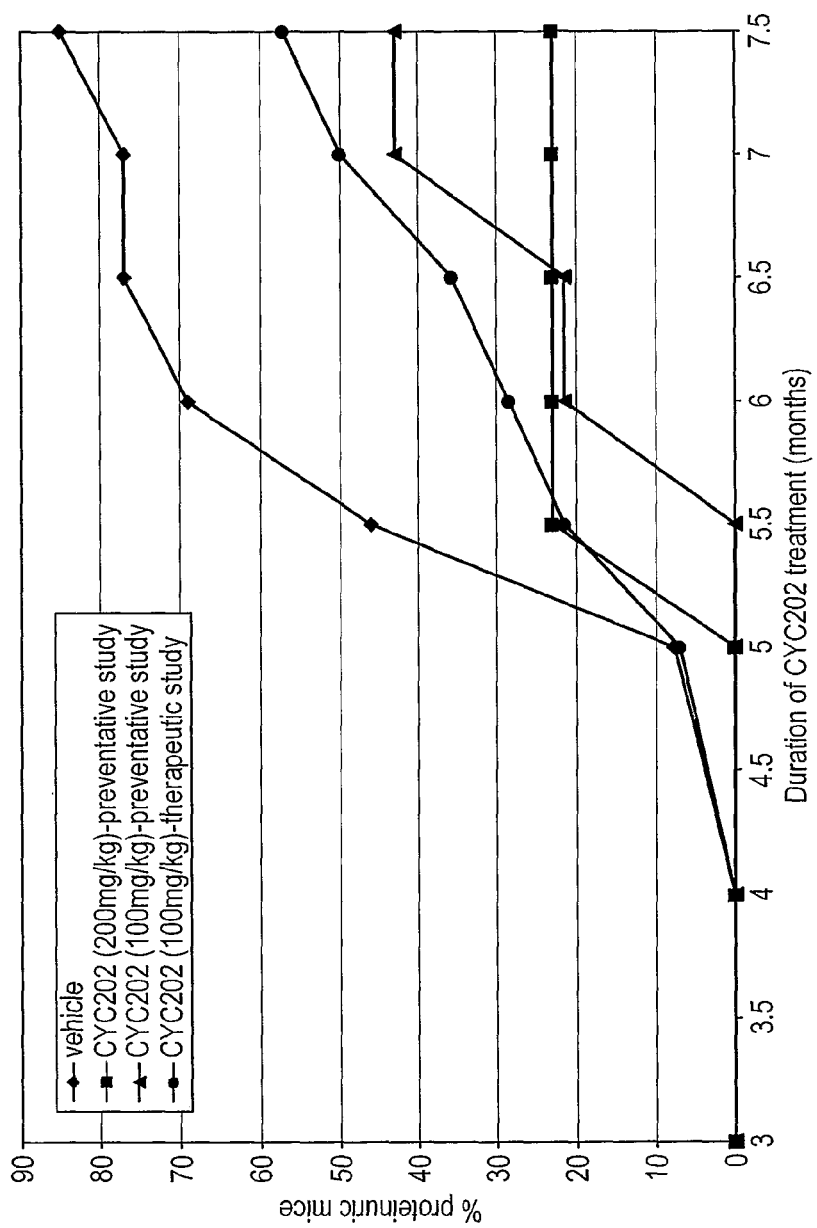
FIG. 2 shows the percentage proteinuric mice against the duration of treatment (months) for NZB/W F1 mice treated with CYC202 at dosages of 100 mg/kg or 200 mg/kg.

Cumulative percentage of mice with heavy proteinuria (>4 mg/day) was evaluated at different stages of the disease in all of the experimental groups. As shown in Table 5, in the vehicle group the percentage of mice with proteinuria progressively increased over time (FIG. 2). At the end of the study the percentage of proteinuric mice was 85%. CYC202 given as a preventive therapy significantly delayed the onset of proteinuria compared to vehicle, in a dose-dependent manner (% proteinuric mice, month 8: 200 mg/kg, 23%, P<0.01 vs vehicle; 100 mg/kg, 43%, P<0.05 vs vehicle). When CYC202 was administered to lupus mice from 5 months of age a tendency toward a reduced percentage of proteinuric mice in respect to vehicle was observed, which however did not reach the statistical significance.

Renal function, assessed by serum BUN, was measured at 5 and 8 months. At 5 months serum BUN levels were within the normal range (<29 mg/dl) in all the experimental groups. In the vehicle group, renal function deteriorated with time and at 8 months 50% of the surviving animals had BUN levels ≥30 mg/dl (Table 6). CYC202 given as preventive therapy resulted in a better renal function of lupus mice, whereas it was not effective when administered late.

Anti-DNA Antibodies

Figure 3:
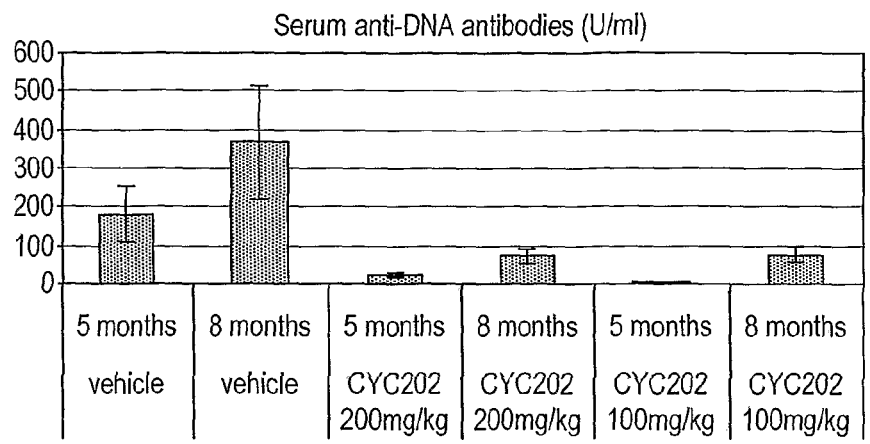
FIG. 3 shows serum anti-DNA antibodies (U/ml) for NZB/W F1 mice treated with CYC202 at 100 mg/kg or 200 mg/kg (versus control vehicle).

Elevated anti-DNA antibody levels are characteristic of NZB/W F1 mice. As shown in Table 7, mice given vehicle exhibited increasing levels of anti-DNA antibodies over time. Either at 5 or 8 months of age, mice treated from 2 months with CYC202 at both doses showed anti-DNA antibody levels significantly lower than vehicle. In the group of mice receiving CYC202 from 5 months anti-DNA antibody concentration was numerically, albeit not significantly lower than vehicle at 8 months (FIG. 3).

Serum Transaminase Levels

Serum ALT and AST levels were measured in NZB/W F1 mice given 200 mg/kg CYC202 from 2 months or 100 mg/kg CYC202 from 5 months. Serum transaminase levels were not modified by treatments and values were similar to those of control mice (Table 8).

Renal Morphology

As shown in Table 9, at the end of the study NZB/W mice given vehicle revealed glomerular changes with intracapillary hypercellularity associated with a focal extracapillary proliferation. Immune type of deposits were detected in the mesangium and on subendothelial aspect of the glomerular basement membrane. Tubular damage and interstitial inflammation were also observed. Treatment from 2 months with CYC202 markedly limited glomerular hypercellularity, immune deposits, and tubulointerstitial damage. These effects were more pronounced when CYC202 was given at the dose of 200 mg/kg. Only a mild effect on renal morphology was observed in mice administered CYC202 from 5 months.

Interstitial Accumulation of Monocytes/Macrophages

Kidneys were analysed for F4/80 positive monocytes/macrophages by immunohistochemical technique. A marked accumulation of F4/80 positive cells was present in the renal interstitium of NZB/W mice given vehicle (Table 10). Preventive treatment with 200 mg/kg CYC202 remarkably reduced the number of F4/80 positive monocytes/macrophages in respect to vehicle. CYC202 at the dose of 100 mg/kg limited albeit not to a statistically significant degree the interstitial accumulation of mononuclear cells. A numerical reduction of F4/80 positive cells was observed in the therapeutic study.

The results of the present project clearly indicate that CYC202 (200 and 100 mg/kg) given as a preventive therapy from 2 months of age, retarded renal manifestation of lupus in NZB/W mice and remarkably prolonged life as compared to animals given vehicle. Specifically, CYC202 delayed the onset of proteinuria and renal function impairment, and limited glomerular and tubulointerstitial changes including the interstitial accumulation of mononuclear cells, the effects being more pronounced at the dose of 200 mg/kg. A remarkable finding of the present study was the reduction of the levels of anti-DNA antibodies by CYC202, which could possibly be attributed to CYC202 effects on T cells which in turn may affect B cells. By in vitro experiments a concentration-dependent inhibition of T cell proliferation induced by PMA and ConA as well as in mixed lymphocyte reaction has been observed. On the other hand there is evidence that in SLE, activated autoimmune T cells specific for histones or nucleosomes may provide help for B cells to differentiate into anti-DNA producing plasma cells (for review see Rekvig, Arthritis & Rheumatism 48: 300-312, 2003).

The administration of CYC202 (100 mg/kg) initiated at 5 months of age resulted in a mild reduction of the percentage of proteinuric mice and of renal damage in respect to vehicle-mice. Survival was not ameliorated.

Example 2

Results

Body Weight

NZB/W F1 mice gained weight during the study. No difference in body weight was observed among the experimental groups.

Survival

NZB/W F1 mice treated with the combination of CYC202 and methylprednisolone (MPS), starting from 5 months of age, survived significantly (P<0.0001) longer than vehicle-mice (Table 11). Notably, at 12 months, when all mice given vehicle died, ten of sixteen animals (62%) treated with the combined therapy were alive. Survival curves of mice receiving the single therapies were not different from that of vehicle group.

Proteinuria

Table 12 shows the cumulative percentage of mice with proteinuria>4 mg/day evaluated at different stages of the disease. The association of CYC202 and MPS significantly delayed the onset of proteinuria compared to vehicle. In the interval from 7 to 10 months the proportion of proteinuric mice in the combined therapy group was significantly lower than in the vehicle group (6.2 to 43.8% versus 40 to 90%). CYC202 or MPS administered as single therapies only partially affected the onset of proteinuria as compared to vehicle, with a significant reduction in the percentage of proteinuric mice being observed at 7.5 months for the CYC202 group.

Renal Function

Renal function, assessed by serum BUN, was measured monthly from 5 (before treatment) to 12 months. Table 13 shows the cumulative percentage of mice with BUN levels ≥30 mg/dl. At 5 months serum BUN levels were within the normal range (i.e. 14 to 29 mg/dl) in all the experimental groups. In the vehicle group, renal function deteriorated with time. Thus, at 8 and 12 months 80% and 100% of animals, respectively, had BUN levels ≥30 mg/dl. By contrast, only 27% and 53% of mice on the combined therapy had impaired renal function at these time points. CYC202 or MPS given alone displayed a less renoprotective effect than when used in combination.

Renal Morphology

Morphological analysis was performed on renal specimens taken from either terminally ill mice at different times or mice sacrificed at 12 months. Data are reported in Table 14. NZB/W mice given vehicle revealed glomerular changes with intracapillary hypercellularity associated with a focal extra-capillary proliferation Immune-type deposits were detected in the mesangium and on the subendothelial aspect of the glomerular basement membrane. Tubular damage and interstitial inflammation were also observed. Treatment with CYC202 plus MPS markedly limited glomerular hypercellularity, immune deposits, and tubulointerstitial damage. A mild effect on renal morphology was observed in mice administered CYC202 or MPS alone.

Interstitial Accumulation of Monocytes/Macrophages

Kidneys were analysed for F4/80 positive monocytes/macrophages by immunohistochemical technique. A marked accumulation of F4/80 positive cells was present in the renal interstitium of NZB/W mice given vehicle (Table 15). The combined administration of CYC202 and MPS resulted in 65% reduction of the number of monocytes/macrophages in respect to vehicle (P<0.01). CYC202 given alone reduced interstitial infiltrates by 33%. In the group of mice treated with MPS alone interstitial accumulation of mononuclear cells was similar to that found in the vehicle group.

By way of summary, the results showed that CYC202 combined with low dose methylprednisolone significantly prolonged the lupus mice lifespan. Notably, the treatment was initiated at a phase of established disease, i.e. 5 months of age, when immune complex deposition is actively taking place. The combined therapy delayed the onset of proteinuria, limited impairment of renal function and development of glomerular hypercellularity, immune deposits and tubulointerstitial changes. An anti-inflammatory effect was also displayed, as indicated by a reduced accumulation of mononuclear cells into the renal interstitium. The administration of CYC202 or methylprednisolone as single therapies resulted in a mild renoprotective effect.

In conclusion, the results of the therapeutic effect of combined CYC202 and low dose MPS in ameliorating the renal manifestation of lupus and prolonging survival in lupus mice with established disease could represent the basis for a new treatment for lupus nephritis.

Examples 3 and 4

Materials and Methods

Selected CDK 2, 7 and 9 inhibitors (transcriptional inhibitors), compounds [1]-[12] were tested in a T cell proliferation assay, chosen as a surrogate assay for effect on anti-nuclear antibodies.

As mentioned above, anti-nuclear antibody production can only be studied in vivo since the production of these antibodies requires a dysfunctional immune system comprising both B and T cells, and a failure to select and destroy immune cells that recognise self. However, in vitro assays for T cell function (for example, a T cell proliferation assay) are appropriate screening tools to identify compounds that may have the ability to modulate the immune response in the complex situation of autoimmune disease. Thus, a T cell proliferation assay is able to provide a measure of the effect of a compound on antinuclear antibodies.

Preparation of Peripheral Blood Mononuclear Cells

Two separate assays were conducted, Examples 3 and 4. Buffy coat blood from three or four healthy donors (Example 3 and 4, respectively) was obtained from Scottish National Blood Transfusion Services and separated by centrifugation in BD Vacutainer™ CPT cell preparation tubes (4 mL draw capacity, with sodium citrate, REF362781) at 300 g for 30 minutes, room temperature (RT). Peripheral blood mononuclear cell (PBMC) layer was recovered by pipetting and pooled in 50 mL centrifuge tubes, then washed twice in 3 volumes Hank's buffered salt solution (w/o $CaCl_2$ and $MgCl_2$, Gibco #14175-053) by centrifuging at 300 g for 15 minutes (RT). PBMCs were resuspended in RPMI 1640 culture medium supplemented with 10% fetal calf serum and the number of viable cells was determined by Trypan Blue exclusion.

Cell Stimulation and Treatment

PBMCs were seeded in 96 well plates at $1 \times 10^5$ cells/well, in 50 µL per well culture medium. As assay control, CCRF-CEM leukaemia and LP-1 multiple myeloma cells were seeded at 4000 and 5000 cells/well in 100 µL/well RPMI 1640 tissue culture medium/10% fetal calf serum (FCS), respectively, and grown without stimulation or compound treatment for the duration of the experiment. All stimulants and compounds were made up to 4× final concentration in tissue culture medium and 25 µL of each drug and stimulant was then added to wells, for a final volume of 100 µL/well. For unstimulated controls, 25 µL tissue culture medium was added to wells instead of stimulant and for untreated cells, 25 µL/well tissue culture medium containing equal volume DMSO (0.1% final) was added. Three adjacent wells were treated for each stimulation/treatment condition and the mean value calculated for analysis.

For Example 3, cells were allowed to settle for 2 hours before stimulating with either 50 µg/mL PHA (Phytohemagglutinin PHA-P, Sigma L9132) or 50/250 ng/mL PMA/I (Phorbol 12-myristate 13-acetate/Ionomycin, Sigma P8139/10634). In addition, PBMCs were stimulated with ConA (Concanavalin A, Sigma C5275) at concentrations ranging from 0.5 µg/mL to 100 µg/mL to identify its stimulatory effect and optimal concentration. For Example 4, PBMCs were stimulated immediately after seeding, with either 50 µg/mL as before or 10 µg/mL ConA.

For Example 3, stimulated and unstimulated PBMCs were treated with compounds [1]-[10] at $IC_{50}$, $2 \times IC_{50}$, $3 \times IC_{50}$ and $4 \times IC_{50}$ concentrations. Compounds were added at two hours before stimulation (time of seeding), at the time of stimulation and two hours after stimulation and cells then incubated at 37° C., 5% $CO_2$, for 50, 48 and 46 hours with compound, respectively, or until 48 hours after stimulation. For Example 4, stimulated PBMCs were treated with the above compounds, plus compounds [11] and [12], with all compounds tested at $0.5 \times IC_{50}$ and $0.25 \times IC_{50}$ in addition to the previous concentrations. Compounds were added immediately after stimulation and cells incubated for 48 and 72 hours. $IC_{50}$s were based on the average 72 hour $IC_{50}$s from in-house cytotoxicity assays on tumour cell panels (Table 16), except for compounds [1] and [3] for which $IC_{50}$s were based on published $IC_{50}$s previously used in-house, as no in-house $IC_{50}$ data was available.

BrdU ELISA and Alamar Blue Assay

Proliferation activity of PBMCs after stimulation and compound treatment was determined by measuring BrdU incorporation, using the Cell Proliferation ELISA, BrdU (colorimetric) kit (Roche #1 647 229). This kit is a non-radioactive replacement method for $^3H$ thymidine incorporation. Cells were labelled with BrdU for two hours prior to harvesting. Plates were then centrifuged for 10 minutes at 300 g (RT), supernatant removed from wells by pipetting and cells dried for 1 hour at 60° C. FixDenat solution was added to plates (100 µL/well) and incubated for 30 minutes, then flicked to remove and anti-BrdU-POD solution added to plates (100 µL/well) and incubated for 90 minutes. After 3 washes with wash solution (200 µL/well), plates were incubated with substrate solution (100 µL/well) for 30 minutes, then 1M $H_2SO_4$ was added (25 µL/well) and optical density read at 450 nM, on an Ascent Fluoroskan plate reader.

Viability of PBMCs was assessed using Alamar Blue reagent (Biosource #DAL1100). Fresh 20% Alamar Blue was made up in culture medium and 100 µL added to each well for a 10% final concentration. Plates were incubated with Alamar Blue at 37°, 5% $CO_2$, for 3 hours prior to harvesting time (48 or 72 hours) and fluorescence then read using excitation wavelength 535 nM and emission wavelength 595 nM, on a Tecan Ultra plate reader.

Example 3

Results

Figure 4:
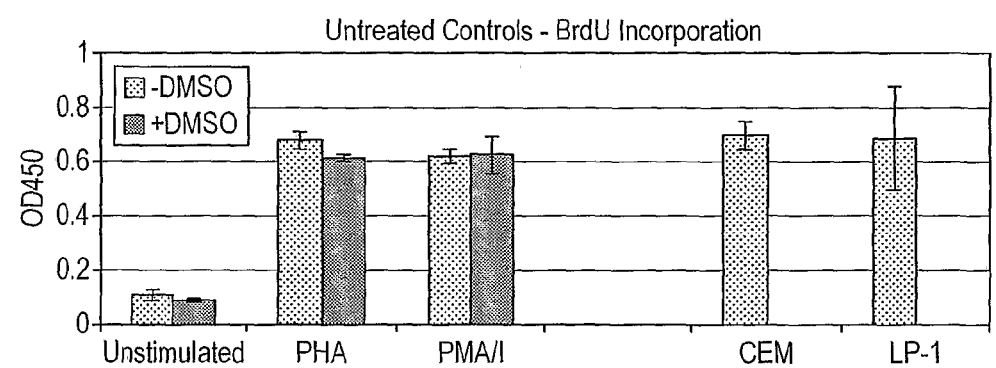
FIG. 4 shows BrdU incorporation (top) and viability (bottom) of unstimulated and stimulated PBMCs and control cells, untreated or treated with DMSO vehicle.
Figure 4:
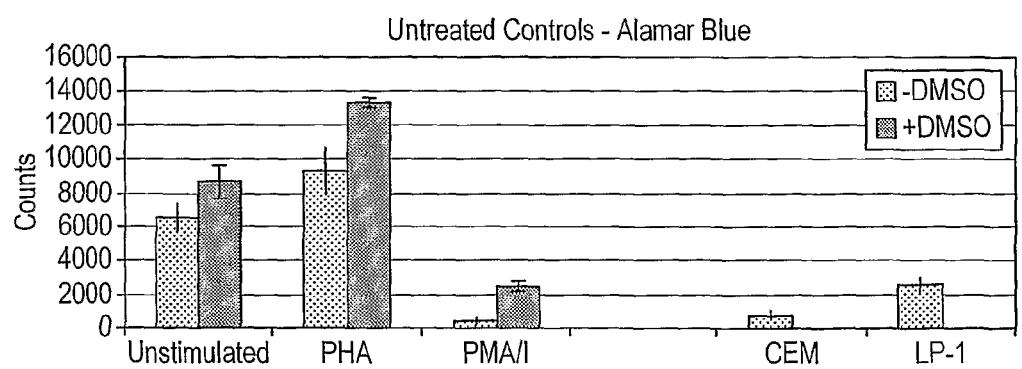
Figure 5:
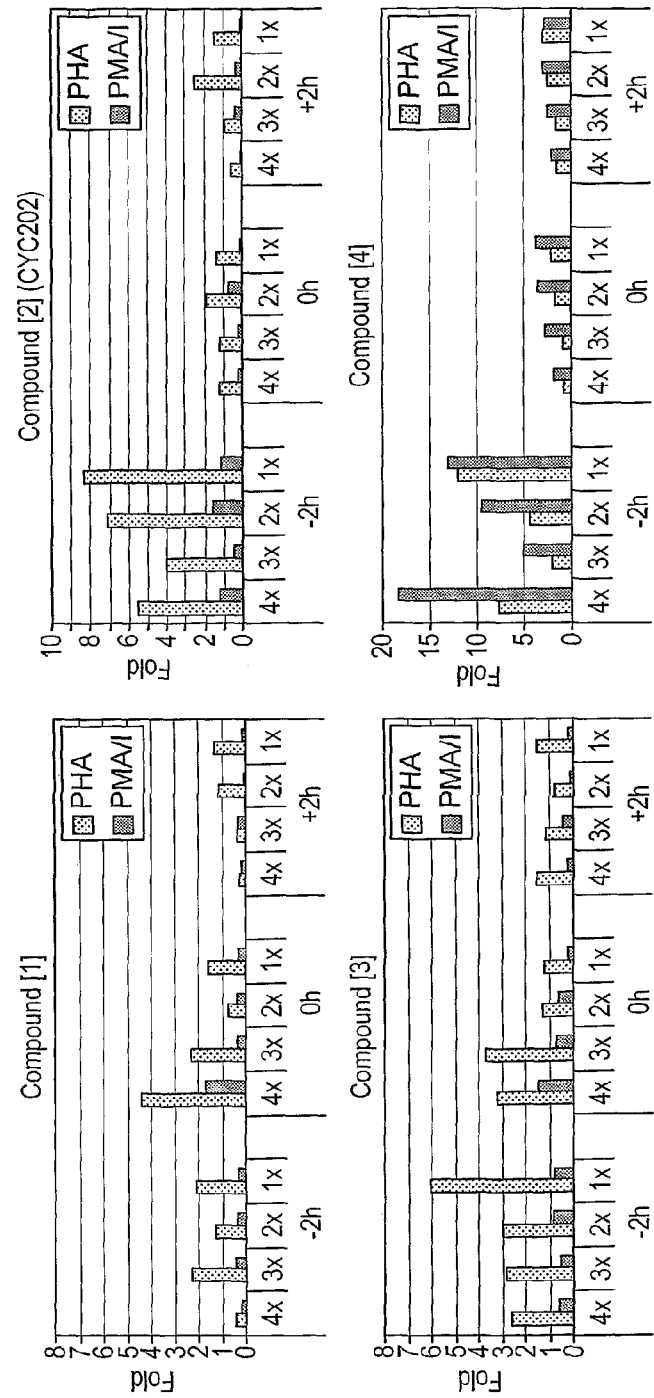
FIG. 5 shows the difference in BrdU incorporation between PBMC cells stimulated with PHA or PMA/I for 48 hour, when treated with DMSO (top left) or compounds at 4×IC50, 3×IC$_{50}$, 2×IC$_{50}$ and IC$_{50}$ concentrations, 2 hours before stimulation (−2 h), at the time of stimulation (0 h) and 2 hours after stimulation (+2 h).
Figure 5:
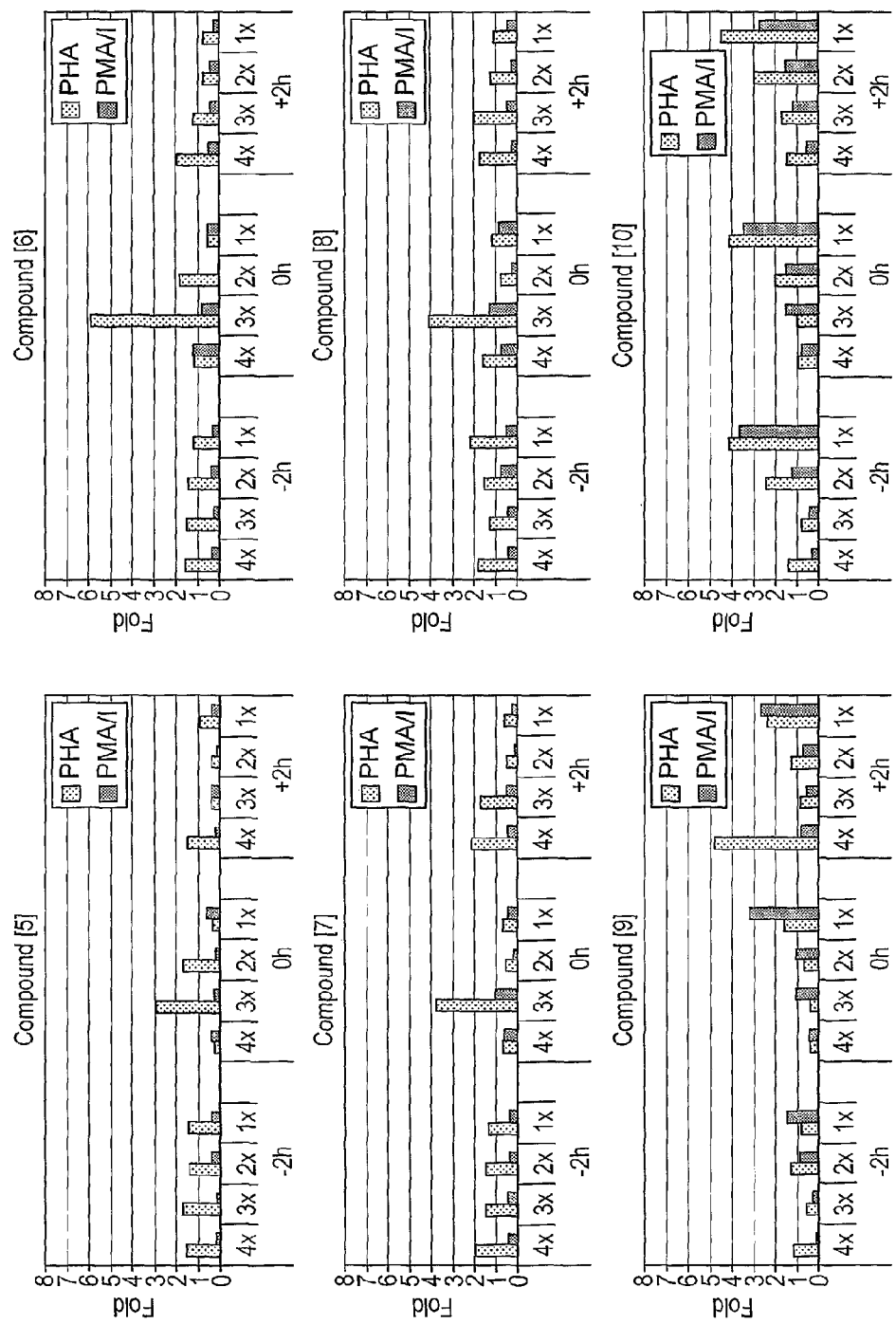
Figure 6:
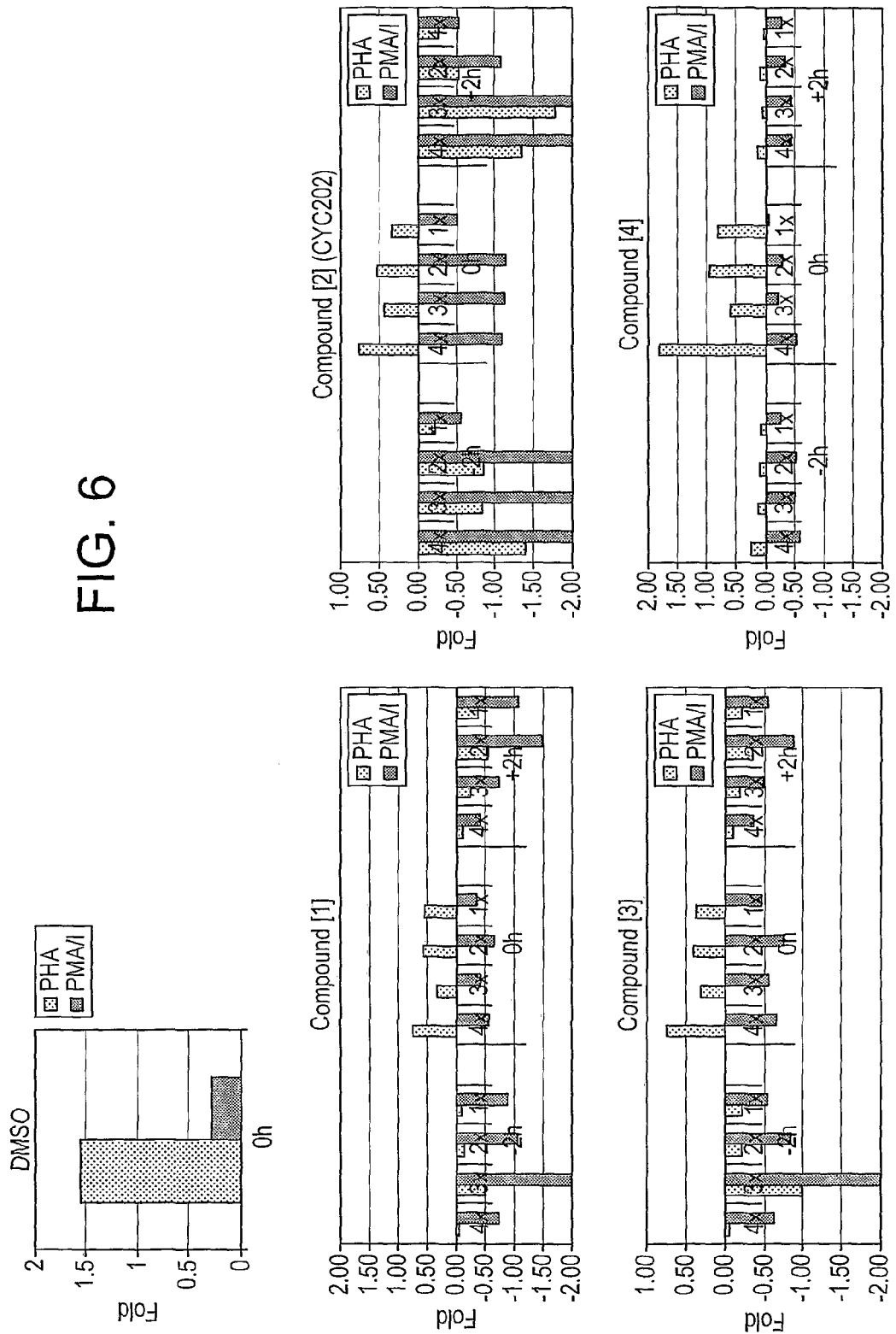
FIG. 6 shows the difference in viability between PBMC cells stimulated with PHA or PMA/I for 48 hour, when treated with DMSO (top left) or compounds at 4×IC$_{50}$, 3×IC$_{50}$, 2×IC$_{50}$ and IC$_{50}$ concentrations, 2 hours before stimulation (−2 h), at the time of stimulation (0 h) and 2 hours after stimulation (+2 h).
Figure 6:
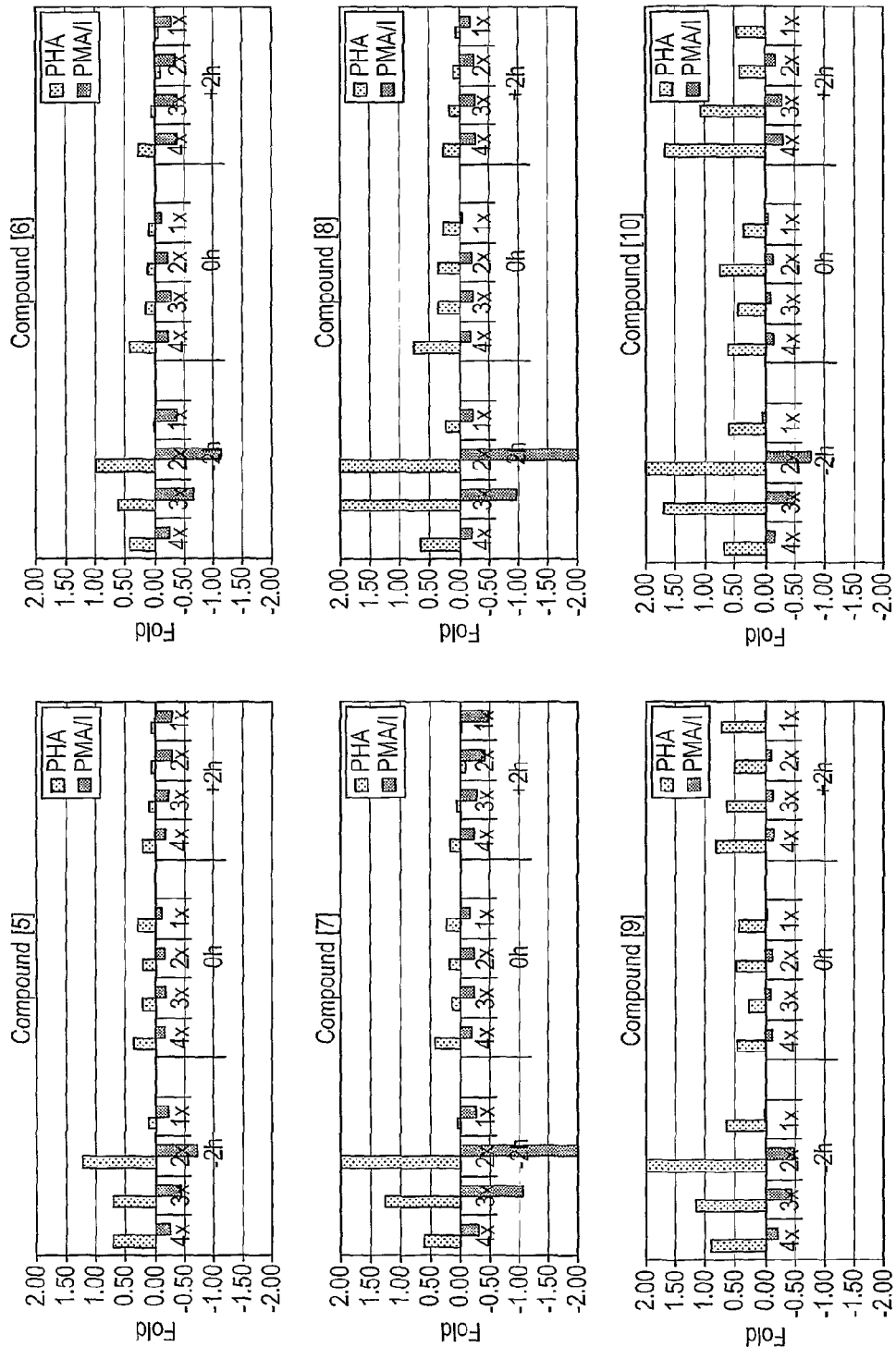

Stimulation with PHA increased BrdU incorporation approximately 7-fold compared to unstimulated cells. Treatment with DMSO vehicle did not affect either BrdU incorporation or viability of PHA stimulated, or unstimulated cells (FIG. 4). As shown in FIG. 5, treatment of PHA stimulated cells with all of the compounds tested reduced BrdU incorporation, in many cases down to the level seen in unstimulated cells. Reduction in BrdU incorporation is evident at concentrations as low as $IC_{50}$ and with the exceptions of compounds [9] and [10], the quantity of BrdU incorporation still remaining does not correlate with compound concentration, together suggesting that the compounds have reached their maximum proliferation inhibitory effect at $IC_{50}$. For compounds [9] and [10] the effect is clearly concentration dependent, with 3-4 times more BrdU incorporation at $IC_{50}$ dropping to unstimulated levels at the higher concentrations.

For most compounds, the time of compound treatment relative to stimulation time did not have a great effect on the level of BrdU incorporation, most likely because the stimulation had not yet taken effect in those first four hours after PBMC seeding. The exceptions to this are compounds [2], [3] and [4] where, surprisingly, there is less reduction in BrdU incorporation with compound pre-treatment (−2 h) than when compound treatment was started at the same time, or after stimulation (FIG. 5).

Similar to PHA treatment, PMA/I stimulation results in around seven fold increase in BrdU incorporation over unstimulated cells, when in the absence of compound (FIG. 5). Treatment with all compounds other than compounds [4], [9] and [10] reduced BrdU incorporation even more than in PHA stimulated cells and generally to levels lower than those seen in unstimulated cells, at all concentrations. PBMCs stimulated with PMA/I and treated with DMSO only showed very low viability in Alamar Blue assay, while BrdU incorporation was increased (FIG. 4), as mentioned above. Similarly, BrdU incorporation still remaining after treatment of PMA/I stimulated cells with compounds [4], [9] and [10] is higher than in PHA stimulated cells, despite negative Alamar Blue values.

Figure 7:
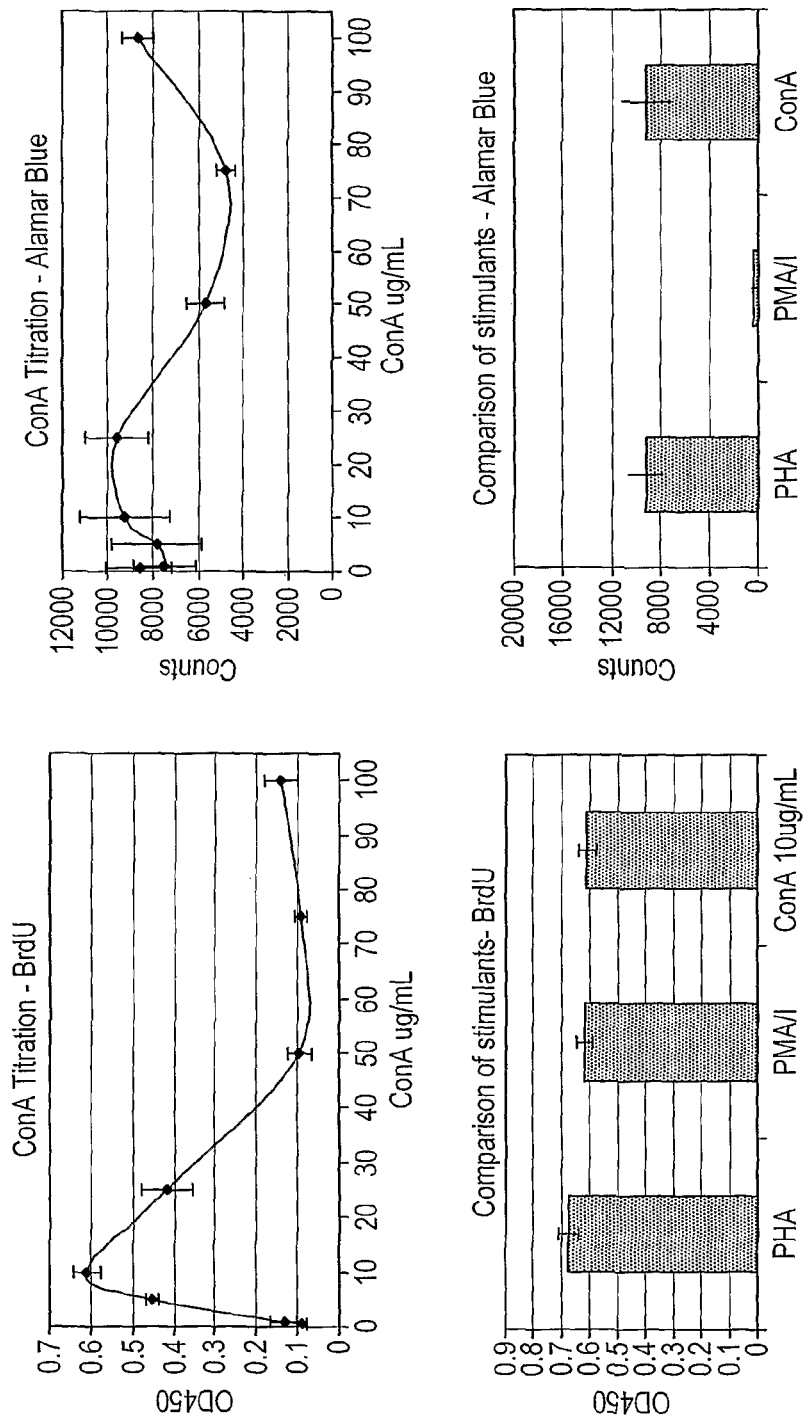
FIG. 7 shows the titration of Concanavalin A shows maximum stimulation with 10 μg/mL (top left), and reduced viability at higher concentrations (top right). Increase in BrdU incorporation is comparable with PHA and PMA/I stimulation (bottom left).

Titration of Concanavalin A shows that ConA stimulates PBMCs in a concentration dependent manner, reaching maximum effect at 10 μg/mL. BrdU incorporation is then reduced to unstimulated levels (higher concentrations), consistent with viability assessment and microscope observations indicating that PBMCs are not viable with the higher ConA concentrations tested. When compared with PHA and PMA/I, stimulation with 10 μg/mL ConA increases BrdU incorporation to a comparable level, or by about 6-fold over unstimulated PBMCs, without reducing viability (FIG. 7).

Example 4

Results

Example 3 concluded that all the compounds tested affect the proliferation activity of stimulated PBMC cells at concentrations as low as $IC_{50}$. A subsequent experiment (Example 4) was carried out to study the concentration dependence of this effect at drug concentrations lower than $IC_{50}$. Treatments were repeated as before, with the addition of treatments at lower concentrations, 0.5× and 0.25×$IC_{50}$, and DMSO control, for all compounds previously tested plus compounds [11] and [12]. Since the time of compound treatment relative to stimulation did not appear to be central for inhibition of proliferation activity, PBMCs were stimulated and compound treated at the same time, immediately after seeding. Cells were stimulated with either PHA as before or with 10 μg/mL ConA.

Figure 8:
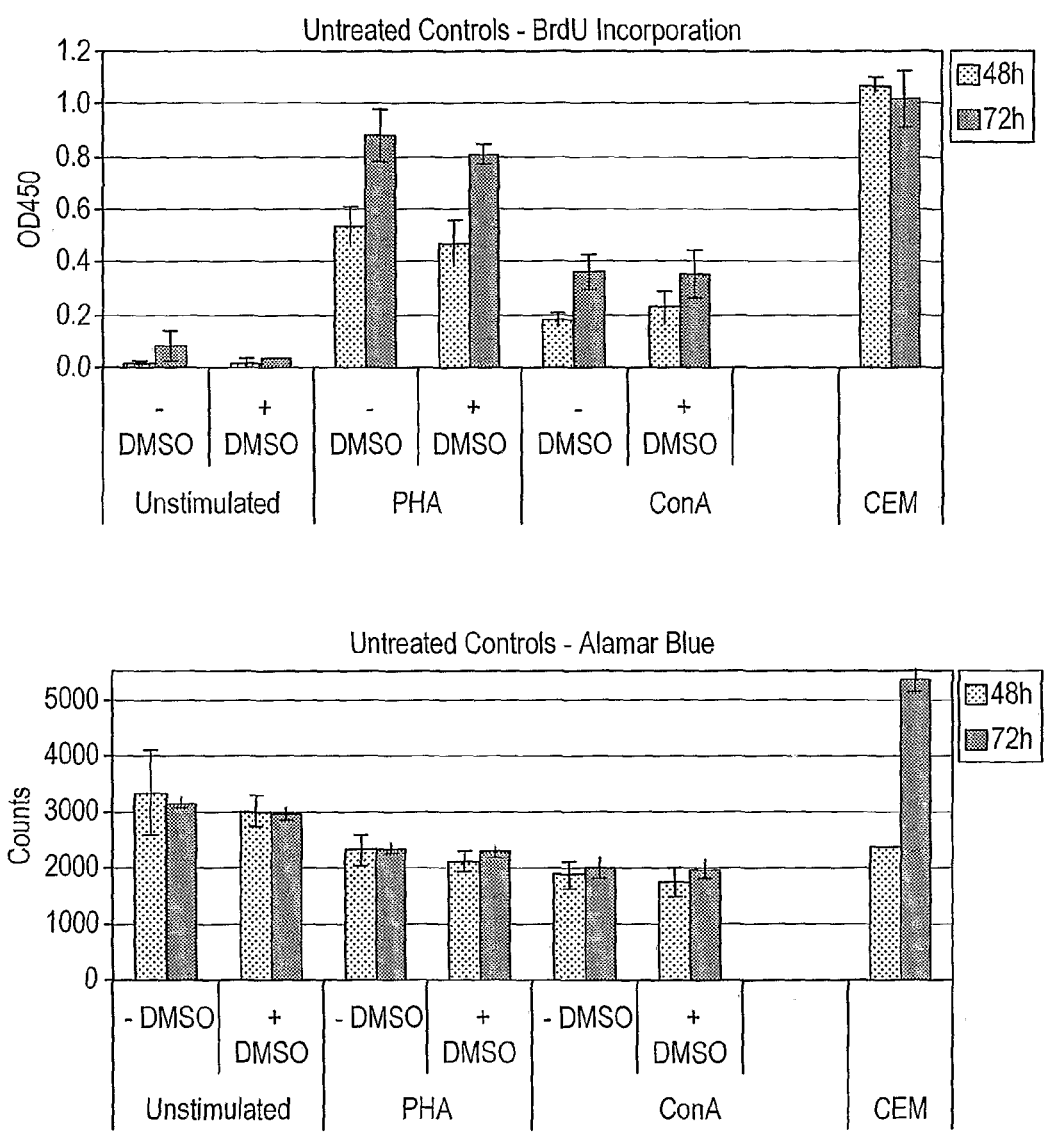
FIG. 8 shows BrdU incorporation (top) and viability (bottom) in PBMCs stimulated with PHA and ConA and unstimulated cells, at 48 and 72 hours treatment with DMSO and untreated.
Figure 9:
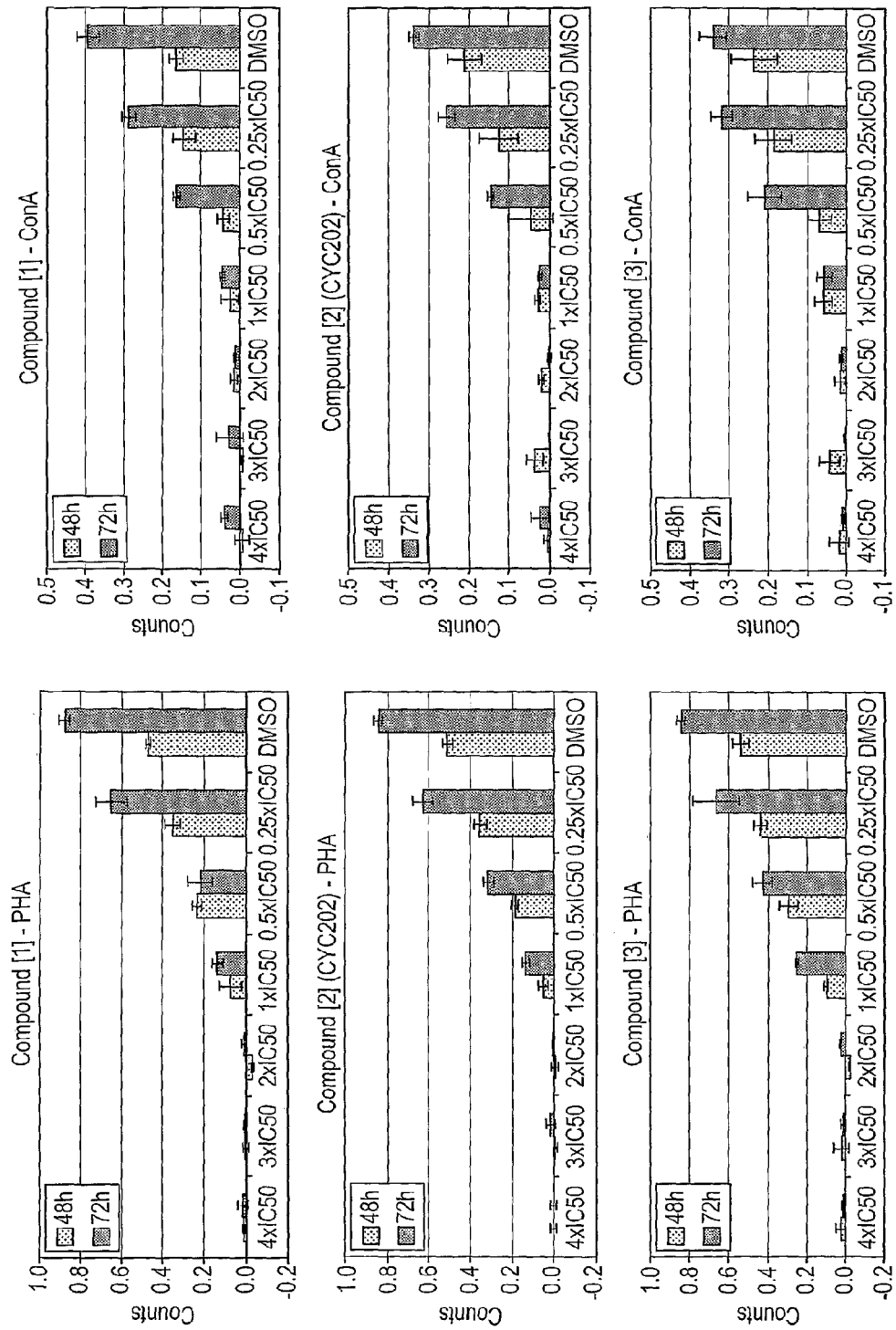
FIG. 9 shows BrdU incorporation in PHA (left) and ConA (right) stimulated PBMCs treated with compounds at $4 \times IC_{50}$, $3 \times IC_{50}$, $2 \times IC_{50}$, $IC_{50}$, $0.5 \times IC_{50}$ and $0.25 \times IC_{50}$ and DMSO control, for 48 and 72 hours.
Figure 9:
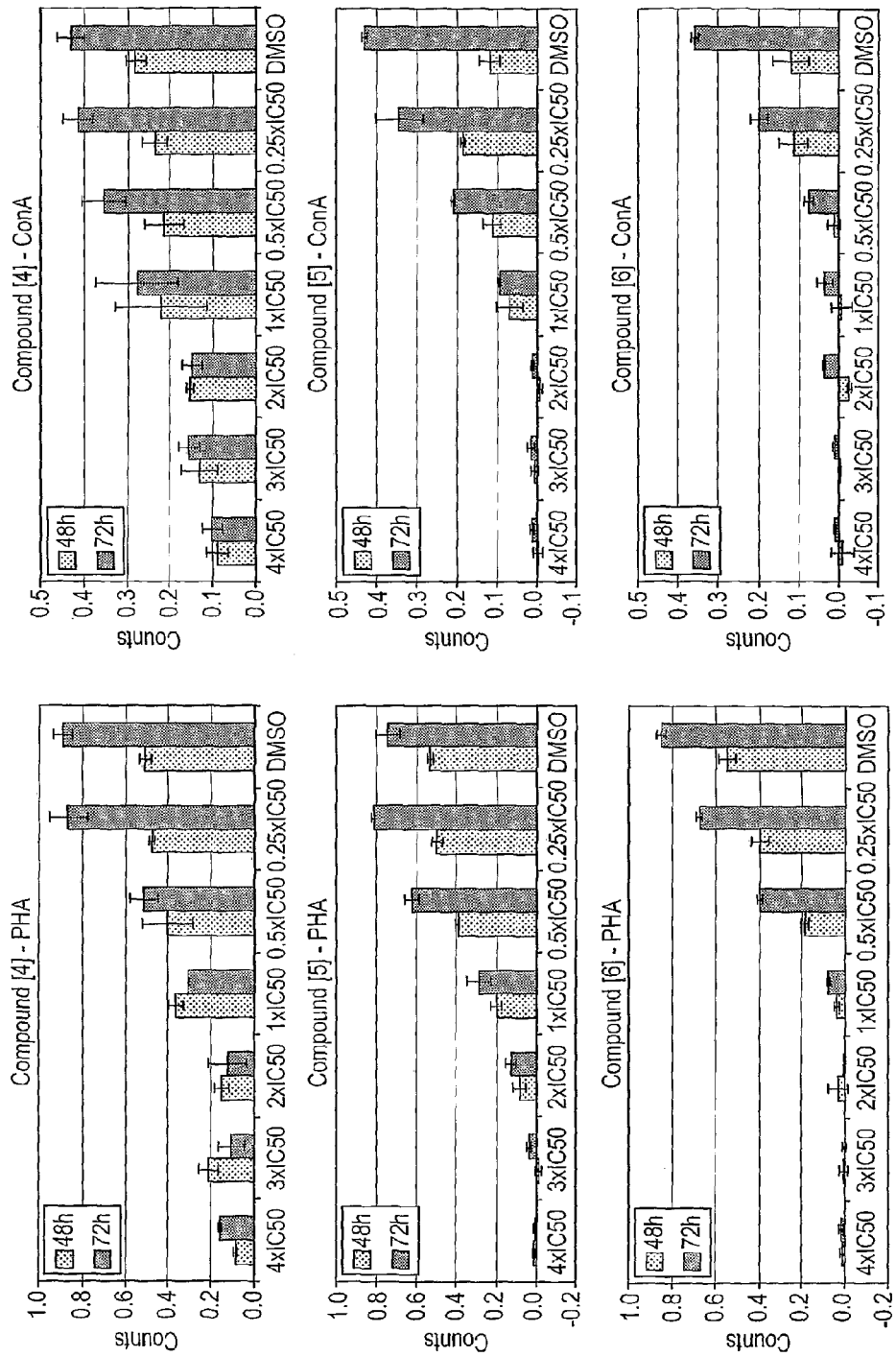
Figure 9:
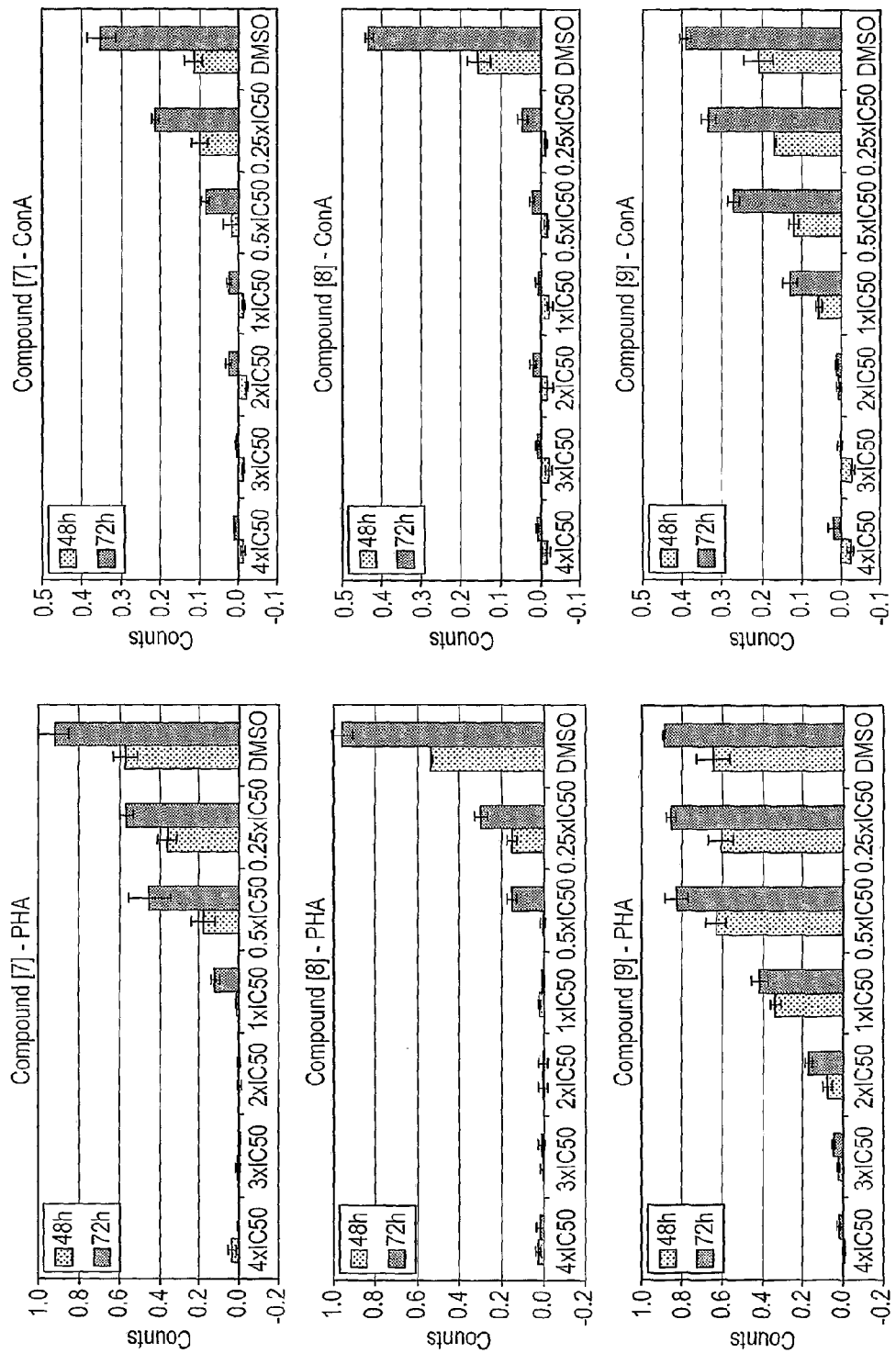
Figure 9:
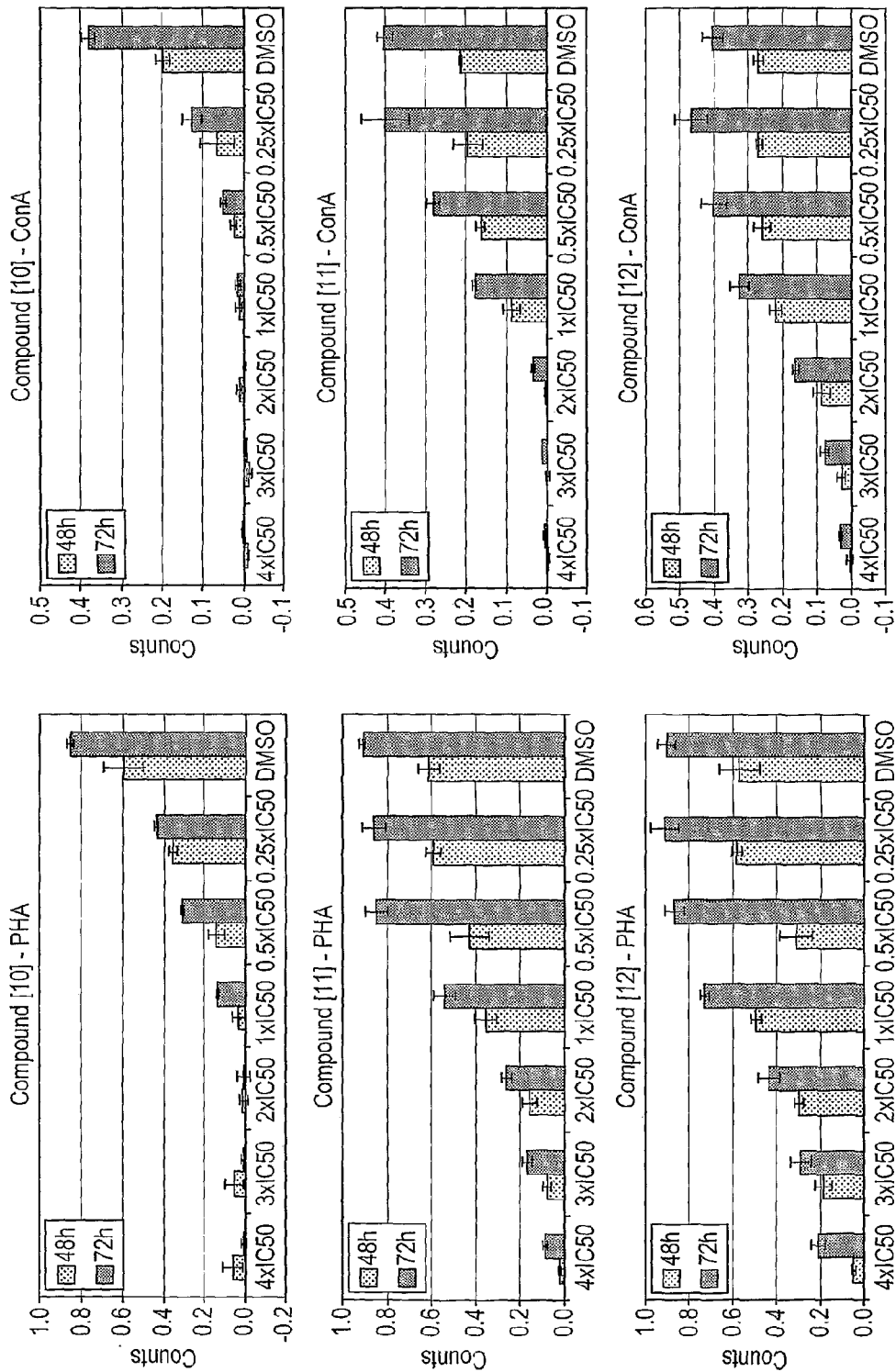
Figure 10:
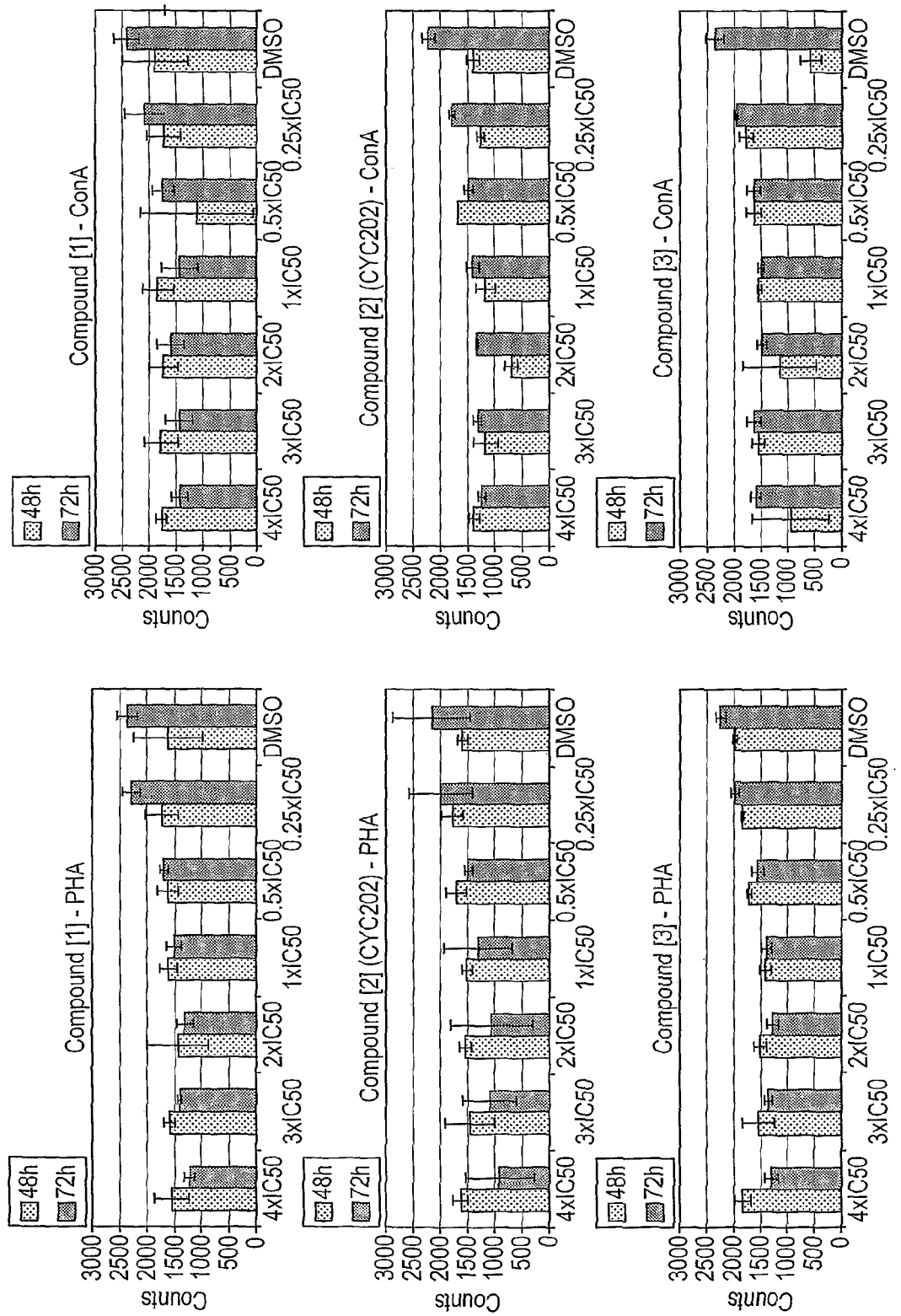
FIG. 10 shows the viability of PHA (left) and ConA (right) stimulated PBMCs treated with compounds at $4 \times IC_{50}$, $3 \times IC_{50}$, $2 \times IC_{50}$, $IC_{50}$, $0.5 \times IC_{50}$ and $0.25 \times IC_{50}$ and DMSO control, for 48 and 72 hours.
Figure 10:
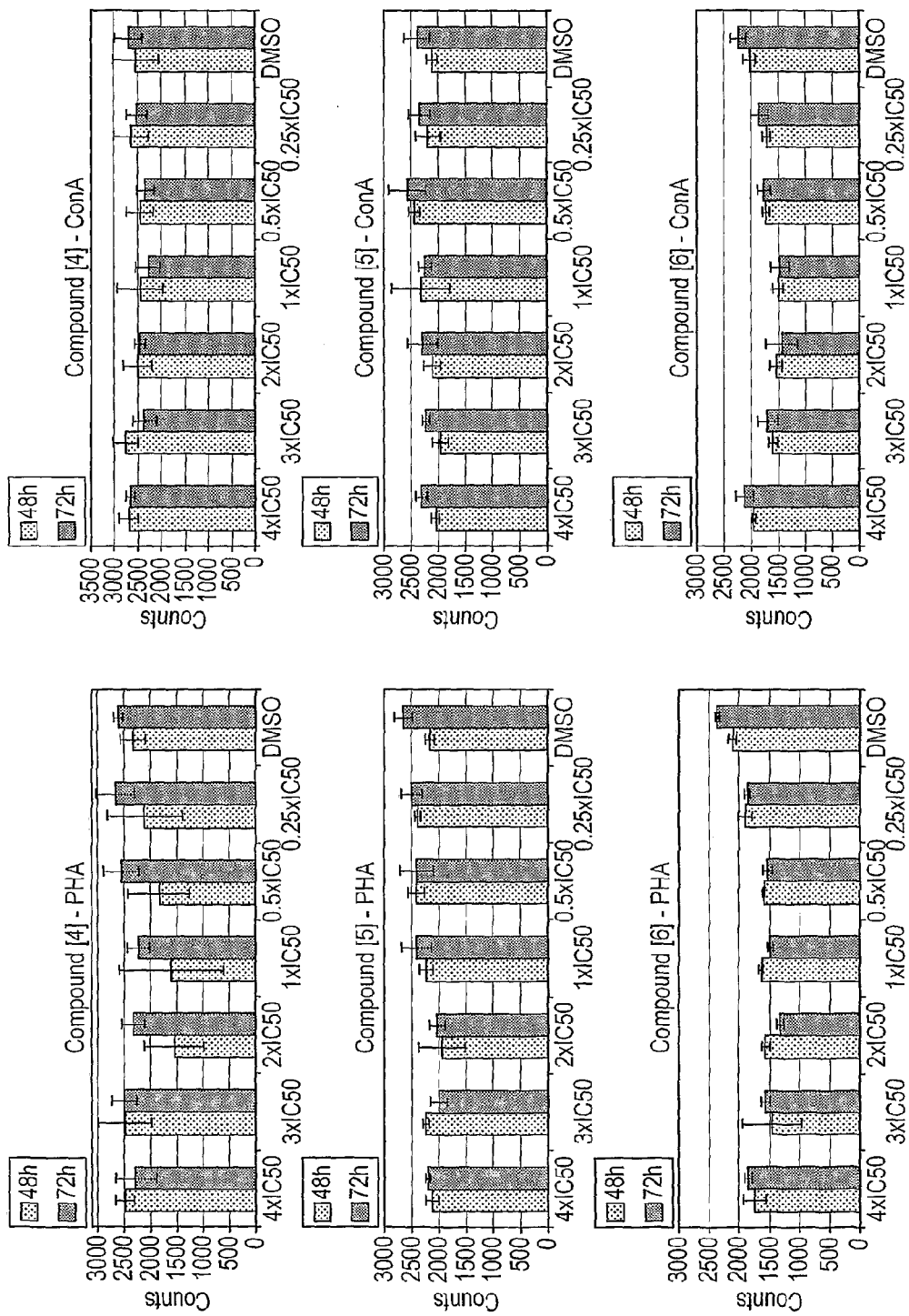
Figure 10:
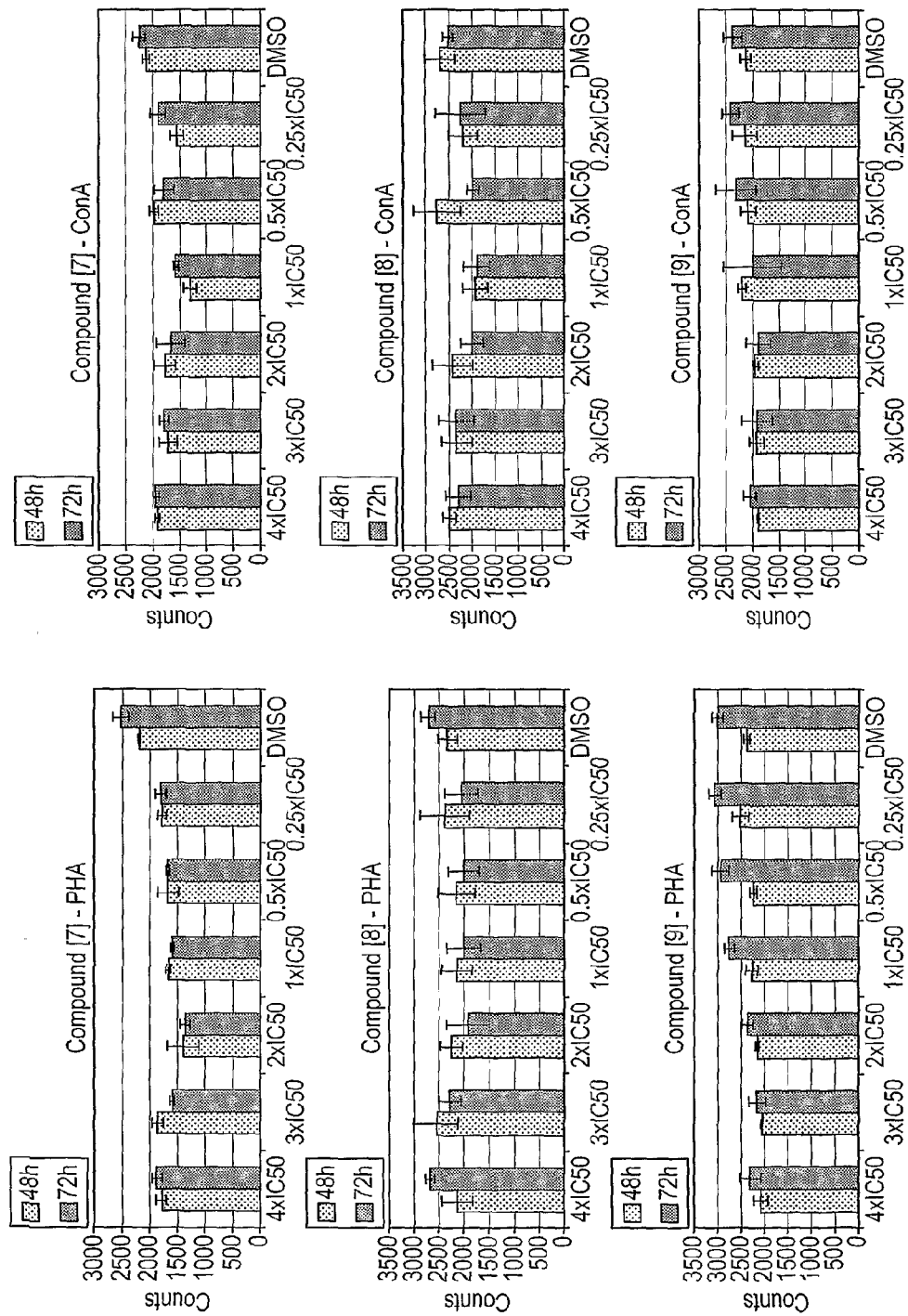
Figure 10:
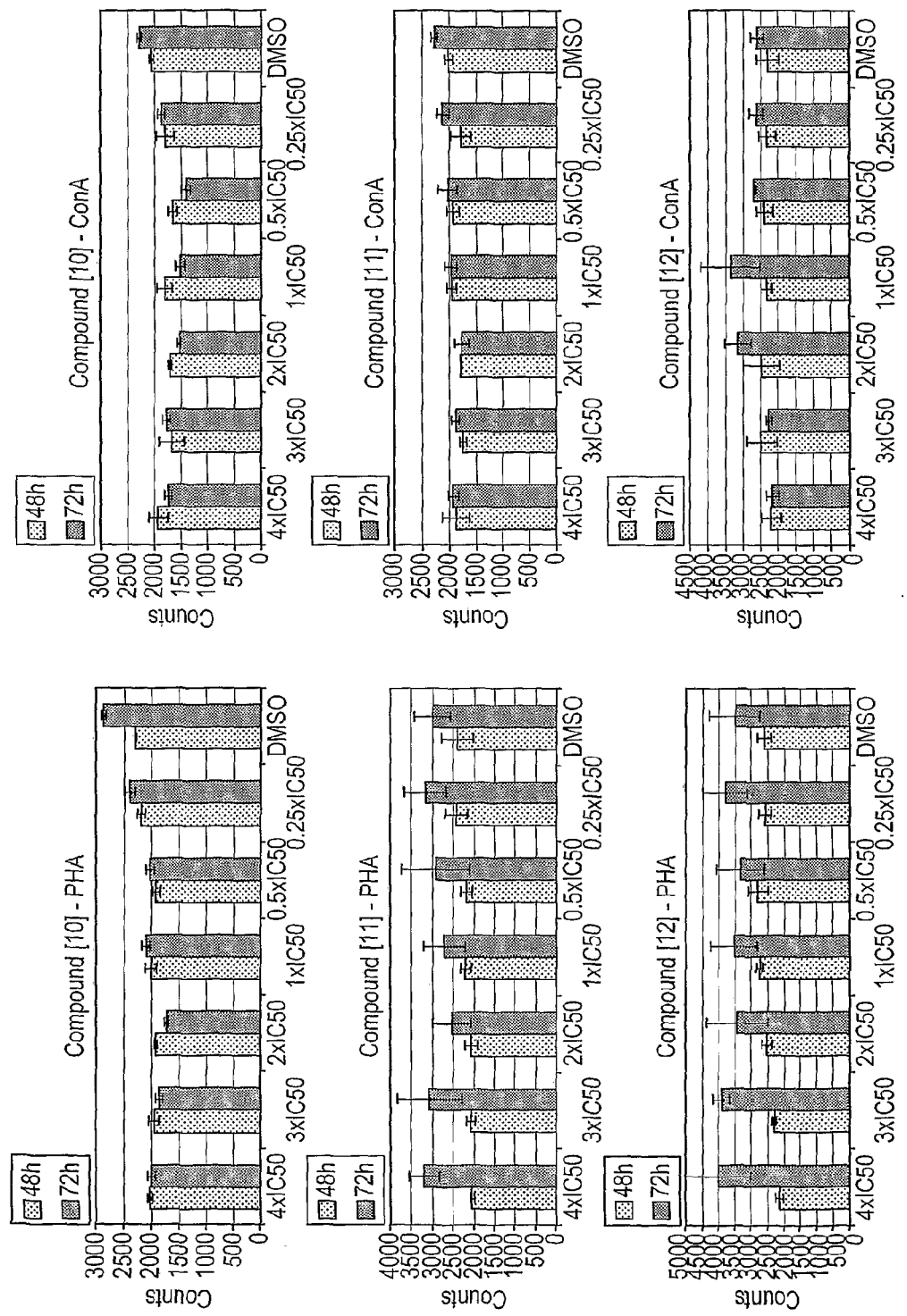

PHA stimulation increased BrdU incorporation of DMSO treated cells by over 20-fold and ConA stimulation by over 10-fold, compared with unstimulated cells, at 48 hours, with further increase at 72 hours, and DMSO vehicle had no effect on either BrdU incorporation or viability (FIG. 8). As shown in FIG. 9, all compounds reduced BrdU incorporation in a concentration dependent manner, most reaching maximum effect at $IC_{50}$ or 2×$IC_{50}$ concentrations, when stimulated with PHA. This confirms the previous observation that concentration dependence was not detected at concentrations above $IC_{50}$, since maximum effect had already been reached. Overall, the same effect was seen for PBMCs stimulated with ConA, although maximum effect was reached at slightly lower concentrations. This may be a result of the fact that BrdU signals drop to background levels at maximum effect and, as signals are generally only half as high for ConA stimulated cells as for PHA stimulated cells, assay sensitivity may be slightly less for the former.

As before, compounds [4], [9] and [10] behave slightly differently from the rest of the compounds. Consistent with the previous experiment, concentration dependency was clearly seen for compounds [9] and [10] at concentrations above $IC_{50}$, which then extended to the lower concentrations. At 4×$IC_{50}$, BrdU incorporation was still decreasing and signals were approaching background levels for ConA stimulated cells, but were slightly higher in PHA stimulated cells. Without wishing to be bound by theory, this suggests that proliferation activity will be completely inhibited as with the other compounds, but higher concentrations are needed to achieve this.

For cells treated with compound [4], BrdU signals do not reduce to background levels with either stimulation, even at 4×$IC_{50}$. Furthermore, little correlation was seen between BrdU incorporation and compound concentration at the higher concentrations, consistent with our previous results. Without wishing to be bound by theory, this suggests that effect of compound [4] on proliferation activity is maximised at around 2×$IC_{50}$ as for most of the other compounds, but the degree of inhibition achieved is lower.

Viability assessment by Alamar Blue assay showed that viability of PBMCs is reduced slightly with stimulation, but is then generally comparable between compound-treated, DMSO-treated and untreated PBMCs. Furthermore, no reduction in Alamar Blue counts is associated with increasing compound concentrations, confirming that the decreasing BrdU incorporation is not caused by cytotoxicity effects of the compounds and is purely representative of inhibition of proliferation activity.

By way of summary, experiments have shown that treatment with any of a set of transcriptional inhibitors alters the effect of PHA or ConA stimulation on T lymphocytes, resulting in a complete inhibition of proliferation activity in a concentration dependent manner. Overall, the same trend is seen for PHA and ConA stimulated cells, although complete inhibition of proliferation appears to be reached at lower drug concentrations in ConA stimulated cells than PHA stimulated cells. This may be an artefact of the lesser total stimulation achieved by ConA than PHA. Most compounds follow the same pattern where some inhibition of proliferation activity is first seen with concentrations as low as 0.25×$IC_{50}$ or 0.5× $IC_{50}$, then reaching complete inhibition at around 2×$IC_{50}$, with some differences as to how rapid the drop in proliferation activity is with increasing compound concentrations. A noteworthy example is compound [7], which reaches complete inhibition at concentrations as low as 0.25×$IC_{50}$. However, the comparison between specific concentrations of different compounds must be approached with caution, since $IC_{50}$ values are based on averages from different cell panels.

Exceptions to the described pattern are seen for compounds [9] and [10], which are needed at higher concentrations than the other compounds to have the same effect, and for compound [4], which follows the same concentration dependence as the others but fails to achieve complete inhibition of proliferation activity at the higher concentrations.

Experiments have shown that PBMC viability is reduced slightly with stimulation but no significant further reduction is associated with compound treatment. More importantly, viability is clearly not dependent on compound concentration and the measured reduction in BrdU incorporation therefore represents true inhibition of proliferation activity and not cytotoxicity of the compounds.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

REFERENCES

Balomenos D. et al. The cell cycle inhibitor p21 controls T-cell proliferation and sex-linked lupus development. Nat. Med, 6:171-176, 2000.
Coma D et al. Mycophenolate mofetil limits renal damage and prolongs life in murine lupus disease. Kidney Int, 51:1583-1589, 1997.
Foster M H. et al. Relevance of systemic lupus erythematosus nephritis animal models to human disease. Semin Nephrol, 19:12-24, 1999.
Gelfand M C et al. Therapeutic studies in NZB/W mice. I. Synergy of azathioprine, cyclophosphamide and methylprednisolone in combination. Arthritis Rheum, 15: 239-246, 1972.
Kewalramani R. et al. Immunopathogenesis of lupus and lupus nephritis:recent insights. Curr Opin Nephrol Hypertens, 11:273-277, 2002.
Von Mulen C. A. et al. Autoantibodies in the Diagnosis of Systemic Rheumatic Diseases. Semin Arthritis Rheum 1995; 24:323-58.
Peutz-Kootstra C. J. et al. Lupus nephritis:lessons from experimental animal models. J Lab Clin Med, 137:244-259, 2001.
Rekvig O P et al. Anti-double-stranded DNA antibodies, nucleosomes, and systemic lupus erythematosus. Arthritis & Rheumatism 48: 300-312, 2003.
Reichlin M. et al. Antinuclear Antibodies: An Overview, Dubois' Lupups Erythematosus $5^{th}$ Edn, eds Wallace D. J. and Hahn B. H., Williams, Wilkins and Baltimore, 1997, p 397-405.
Shankland S. J. et al. Cell cycle regulatory proteins in renal disease: role in hypertrophy, proliferation, and apoptosis. Am J Physiol Renal Physiol, 278:F515-F529, 2000.
Van Venrooij W. J. et al. Manual of Biological Markers of Disease, Section B: Autoantigens. Kluwer Academic Publishing, 1994.
Xu L. et al. Human lupus T cells resist inactivation and escape death by upregulating COX-2. Nature Medicine, 10:411-415, 2004.
Zoja C. et al. Renal expression of monocyte chemoattractant protein-1 in lupus autoimmune mice. J Am Soc Nephrol 8:720-729, 1997.
Zoja C. et al. Bindarit retards renal disease and prolongs survival in murine lupus autoimmune disease. Kidney Int, 53:726-734, 1998.
Zoja C. et al. Mycophenolate mofetil combined with a cyclooxygenase-2 inhibitor ameliorates murine lupus nephritis. Kidney Int, 60:653-663, 2001.

TABLE 1

Body Weight

|  | 2 | 3 | 4 | 5 | 6 | 7 | 8 months |
|---|---|---|---|---|---|---|---|
| Vehicle | 27.69 ± 0.61 | 27.85 ± 0.59 | 28.31 ± 0.56 | 28.08 ± 0.79 | 29.91 ± 0.65 | 31.60 ± 0.75 | 31.75 ± 1.11 |
| CYC202 (200 mg/kg) Preventive study | 27.85 ± 0.72 | 28.00 ± 0.68 | 28.54 ± 0 0.45 | 28.92 ± 0.35 | 31.58 ± 0.43 | 30.82 ± 0.35 | 31.60 ± 0.52 |
| CYC202 (100 mg/kg) Preventive study | 27.93 ± 0.62 | 27.86 ± 0.52 | 28.07 ± 0.57 | 28.64 ± 0.57 | 30.23 ± 0.67 | 31.50 ± 0.87 | 30.78 ± 0.91 |
| CYC202 (100 mg/kg) Therapeutic study | 26.71 ± 0.74 | 28.14 ± 0.69 | 29.43 ± 1.01 | 29.71 ± 0.82 | 31.45 ± 0.96 | 30.80 ± 1.69 | 29.80 ± 1.46 |

Values are expressed as mean ± SE

TABLE 2

Food Intake

|  | 2 | 2.5 | 3 | 3.5 | 4 | 4.5 | 5 months |
|---|---|---|---|---|---|---|---|
| Vehicle | 3.77 ± 0.28 | 4.31 ± 0.17 | 4.15 ± 0.22 | 3.62 ± 0.35 | 3.54 ± 0.35 | 3.31 ± 0.35 | 3.50 ± 0.15 |
| CYC202 (200 mg/kg) Preventive study | 3.54 ± 0.29 | 4.08 ± 0.08 | 4.00 ± 0.11 | 4.08 ± 0.21 | 4.00 ± 0.16 | 4.00 ± 0.18 | 3.92 ± 0.29 |
| CYC202 (100 mg/kg) | 3.69 ± 0.33 | 3.77 ± 0.23 | 3.92 ± 0.18 | 4.08 ± 0.18 | 3.92 ± 0.26 | 3.85 ± 0.30 | 3.85 ± 0.22 |

TABLE 2-continued

Food Intake

|  | 2 | 2.5 | 3 | 3.5 | 4 | 4.5 | 5 months |
|---|---|---|---|---|---|---|---|
| Preventive study |  |  |  |  |  |  |  |

Values are expressed as mean ± SE

TABLE 3

Water intake

|  | 2 | 2.5 | 3 | 3.5 | 4 | 4.5 | 5 months |
|---|---|---|---|---|---|---|---|
| Vehicle | 4.62 ± 0.33 | 5.00 ± 0.30 | 5.00 ± 0.30 | 4.54 ± 0.39 | 5.15 ± 0.15 | 5.00 ± 0.23 | 5.08 ± 0.23 |
| CYC202 (200 mg/kg) Preventive study | 5.31 ± 0.26 | 4.77 ± 0.20 | 4.92 ± 0.18 | 5.08 ± 0.21 | 4.85 ± 0.27 | 4.38 ± 0.43 | 4.23 ± 0.28 |
| CYC202 (100 mg/kg Preventive Study | 6.64 ± 0.29 | 5.14 ± 0.40 | 4.21 ± 0.28 | 5.00 ± 0.28 | 5.57 ± 0.20 | 4.43 ± 0.20 | 3.93 ± 0.22 |

Values are expressed as mean ± SE

TABLE 4

Survival %

|  | 3 | 4 | 5 | 5.5 | 6 | 6.5 | 7 | 7.5 | 8 months |
|---|---|---|---|---|---|---|---|---|---|
| Vehicle | 100 | 100 | 92 | 85 | 85 | 62 | 38 | 31 | 31 |
| CYC202 (200 mg/kg) Preventive study | 100 | 100 | 100 | 92 | 92 | 92 | 85 | 77 | 77 |
| CYC202 (100 mg/kg) Preventive study | 100 | 100 | 100 | 100 | 93 | 71 | 71 | 71 | 71 |
| CYC202 (100 mg/kg) Therapeutic study | 100 | 100 | 100 | 93 | 71 | 64 | 36 | 36 | 36 |

TABLE 5

Cumulative precentage of proteinuric mice

|  | 3 | 4 | 5 | 5.5 | 6 | 6.5 | 7 | 7.5 |
|---|---|---|---|---|---|---|---|---|
| Vehicle | 0 | 0 | 7.7 | 46.0 | 69.0 | 77.0 | 77.0 | 85 |
| CYC2002 (200 mg/kg) | 0 | 0 | 0 | 23.1 | 23.1* | 23.1** | 23.1** | 23.1** |
| CYC202 (100 mg/kg) | 0 | 0 | 0 | 0** | 21.4* | 21.4** | 42.9 | 42.9* |
| CYC202 (100 mg/kg) | 0 | 0 | 7.1 | 21.4 | 28.5 | 35.7 | 50.0 | 57 |

*P < 0.05,
**P < 0.01 vs vehicle

TABLE 6

Renal function assessed by serum BUN

|  | 8 Months |  |
|---|---|---|
| Vehicle | 50% (43-169 mg/dl) |  |
| CYC202 (200 mg/kg) Preventive study | 30% (36-88 mg/dl) |  |
| CYC202 (100 mg/kg) Preventive study | 33% (31-43 mg/dl) |  |
| CYC202 (100 mg/kg) Therapeutic study | 40% (30-111 mg/dl) |  |

TABLE 7

Serum anti-DNA antibodies (U/ml)

| Vehicle | 5 months | 181.30 ± 74.15 |
|---|---|---|
|  | 8 months | 367.29 ± 149.02 |
| CYC202 (200 mg/kg) Prventive study | 5 months | 24.20 ± 6.52 |
|  | 8 months | 73.39 ± 21.13* |
| CYC202 (100 mg/kg) Preventive study | 5 months | 4.04 ± 0.76** |
|  | 8 months | 76.55 ± 21.40* |
| CYC202 (100 mg/kg) Therapeutic study | 8 months | 153.22 ± 90.73 |
| Control (CD-1 mice) |  | 6.43 ± 1.34 |

Values are expressed as mean ± SE
*P < 0.05,
**P < 0.01 vs vehicle at corresponding time.

TABLE 8

Serum Transaminase (IU/L)

|  | AST (IU/L) | ALT (IU/L) |
|---|---|---|
| CYC202 (200 mg · kg) Preventive study | 62.89 ± 4.70 | 36.44 ± 4.04 |
| CYC202 (100 mg/kg) Therapeutic study | 74.40 ± 1.72 | 36.00 ± 2.45 |
| Control (CD-1 mice) | 78.00 ± 2.28 | 36.40 ± 2.64 |

Values are expressed as mean ± SE

TABLE 9

Renal Histology

| | Intracapillary hypercellularity | Extracapillary Proliferation | Glomeruli deposits | Tubulointerstital Damage |
|---|---|---|---|---|
| Vehicle | 2.00 ± 0.44 | 1.00 ± 0.38 | 1.14 ± 0.34 | 0.71 ± 0.23 |
| CYC202 (200 mg/kg) Preventive study | 0.36 ± 0.15**°° | 0.18 ± 0.18 | 0.27 ± 0.19* | 0.25 ± 0.16*° |
| CYC202 (100 mg/kg) Preventive study | 0.92 ± 0.23* | 0.67 ± 0.26 | 0.92 ± 0.23 | 0.46 ± 0.17 |
| CYC202 (100 mg/kg) Therapeutic study | 1.29 ± 0.18 | 0.57 ± 0.20 | 1.14 ± 0.26 | 0.61 ± 013 |

Values are expressed as mean ± SE.
*P < 0.05,
**P < 0.05,
°°P < 0.01 vs CYC202 (100 mg/kg) from 5 months

TABLE 10

F4/80 positive monocytes/macrophages in the renal interstitium

| | 8 months |
|---|---|
| Vehicle | 29.68 ± 5.97# |
| CYC202 (200 mg/kg) Preventive study | 8.56 ± 1.94°*# |
| CYC202 (100 mg/kg) Preventive study | 18.26 ± 4.89# |
| CYC202 (100 mg/kg) Therapeutic study | 21.87 ± 5.13# |
| Control | 0.25 ± 0.25 |

TABLE 11

Survival %

| | 5 | 5.5 | 6 | 6.5 | 7 | 7.5 | 8 | 8.5 | 9 | 9.5 | 10 | 10.5 | 11 | 11.5 | 12 m |
|---|---|---|---|---|---|---|---|---|---|---|---|---|---|---|---|
| | | | | | | | (pre-treatment) | | | | | | | | |
| Vehicle | 100 | 100 | 100 | 90 | 90 | 90 | 60 | 30 | 20 | 10 | 10 | 10 | 10 | 10 | 0 |
| CYC202 (200 mg/kg) | 100 | 100 | 93 | 87 | 87 | 80 | 80 | 67 | 53 | 40 | 34 | 20 | 13 | 13 | 13 |
| MPS (1.5 mg/kg) | 100 | 100 | 100 | 92 | 75 | 67 | 67 | 67 | 42 | 42 | 33 | 33 | 33 | 33 | 33 |
| CYC202 + MPS | 100 | 100 | 100 | 94 | 94 | 94 | 94 | 94 | 81 | 75 | 69 | 62 | 62 | 62 | 62 |

Treatments started at 5 months of age. CYC202 + MPS significantly (P < 0.0001) prolonged life in respect to vehicle.

TABLE 12

Cumulative percentage of mice with proteinuria >4 mg/day

| | 5 | 5.5 | 6 | 6.5 | 7 | 7.5 | 8 | 8.5 | 9 | 9.5 | 10 | 10.5 | 11 | 11.5 | 12 m |
|---|---|---|---|---|---|---|---|---|---|---|---|---|---|---|---|
| | | | | | | | (pre-treatment) | | | | | | | | |
| Vehicle | 0 | 10 | 20 | 30 | 40 | 90 | 90 | 90 | 90 | 90 | 90 | 90 | 90 | 90 | 90 |
| CYC202 (200 mg/kg) | 0 | 0 | 6.7 | 26.7 | 26.7 | 46.6* | 66.6 | 66.6 | 73.3 | 73.3 | 73.3 | 73.3 | 73.3 | 73.3 | 73.3 |
| MPS (1.5 mg/kg) | 0 | 0 | 16.7 | 33.3 | 33.3 | 50 | 75 | 75 | 75 | 75 | 75 | 75 | 75 | 75 | 75 |
| CYC202 + MPS | 0 | 6.2 | 6.2 | 6.2 | 6.2* | 25** | 37.5* | 43.8* | 43.8* | 43.8* | 43.8* | 50 | 56.2 | 56.2 | 56.2 |

Each point reflects the current level of proteinuria in surviving mice as well as the last measurement in deceased mice.
0.05,**p < 0.01vs vehicle.

TABLE 13

Renal Function - Cumulative % mice with BUN >30 mg/dl

| | 5 | 6 | 7 | 8 | 9 | 10 | 11 | 12 months |
|---|---|---|---|---|---|---|---|---|
| Vehicle | 0 | 10% | 40% | 80% | 90% | 90% | 90% | 100% |
| CYC202 (200 mg/kg) | 0% | 7% | 15% | 43% | 57% | 64% | 64% | 64% |
| MPS (1.5 mg/kg) | 0% | 0% | 17% | 42% | 50% | 58% | 58% | 67% |
| CYC202 + MPS | 0% | 0% | 0% | 27% | 40% | 40% | 47% | 53% |

BUN levels >30 mg/dl were considered abnormal (normal range: 14-29 mg/dl)

TABLE 14

Renal Histology

| | Intracapillary hypercellularity | GLOMERULI extracapillary proliferation | immune deposits | TUBULO-INTERSTITIAL DAMAGE |
|---|---|---|---|---|
| Vehicle | 1.60 ± 0.24 | 1.00 ± 0.00 | 2.20 ± 0.37 | 1.70 ± 0.09 |
| CYC202 (200 mg/kg) | 1.14 ± 0.26 | 0.86 ± 0.14 | 1.43 ± 0.30 | 1.29 ± 0.23 |
| MPS (1.5 mg/kg) | 1.40 ± 0.40 | 0.80 ± 0.20 | 1.80 ± 0.20 | 1.20 ± 0.14 |
| CYC202 + MPS | 0.70 ± 0.30 | 0.30 ± 0.15* | 0.90 ± 0.23*° | 0.45 ± 0.21** |

Values are expressed as mean score ± SE.
*$p < 0.05$,
**$p < 0.01$ vs vehicle;
°$p < 0.05$ vs MPS.

TABLE 15

F4/80 monocytes/macrophages in the renal interstitium (Cells/HPF)

| | |
|---|---|
| Vehicle | 61.5 ± 4.6 |
| CYC202 (200 mg/kg) | 41.4 ± 8.6 |
| MPS (1.5 mg/kg) | 57.2 ± 10.5 |
| CYC202 + MPS | 21.8 ± 4.8**° |

Values are expressed as mean ± SE. HPF = high power field.
**$p < 0.01$ vs vehicle,
°$p < 0.05$ vs < PS
Control CD-1 mice range: 0-4 cells/HPF

TABLE 16

Average 72 hours $IC_{50}$ values (μM) for in-house cell panel and rounded $IC_{50}$ value used, for ease of calculation

| Compound | $IC_{50}$ Average | Number of Cell lines | $IC_{50}$ Used |
|---|---|---|---|
| 1 | 27* | 1* | 25* |
| 2 | 16.45 | 62 | 16 |
| 3 | 56* | 1* | 50* |
| 4 | 1.04 | 47 | 1 |
| 5 | 1.43 | 13 | 1.5 |
| 6 | 10.4 | 13 | 10 |
| 7 | 5.31 | 18 | 5 |
| 8 | 0.876 | 35 | 1 |
| 9 | 0.250 | 6 | 0.25 |
| 10 | 0.753 | 11 | 1 |
| 11 | 0.291 | 7 | 0.5 |
| 12 | 0.353 | 7 | 0.5 |

*No in-house cytotoxicity data available, $IC_{50}$s published for HCT116 cells in Raynaud et al. *Clin Cancer Res* 11 (13): 4875-87, 2005.

TABLE 17

Average $IC_{50}$ values (μM) for compounds against CDK/cyclin and Aurora enzymes from in-house kinase assays

| Compound | CDK1B | CDK2A | CDK2E | CDK4D1 | CDK6D3 | CDK7H | CDK9T1 | AurA | AurB |
|---|---|---|---|---|---|---|---|---|---|
| 1 | >100 | 8.84 | 0.946 | 45.7 | n/a | 0.603 | 2.03 | n/a | n/a |
| 2 | 17.5 | 2.80 | 0.208 | 27.5 | 55.5 | 0.438 | 1.04 | >100 | n/a |
| 3 | >100 | 83.08 | 7.67 | >100 | n/a | >20 | 2.72 | n/a | n/a |
| 4 | 7.46 | 1.05 | 0.505 | 2.82 | 1.04 | 8.57 | 1.88 | 0.038 | 0.030 |
| 5 | 15.9 | 1.24 | 0.931 | 2.75 | 1.94 | 27.0 | 2.71 | 0.051 | 0.023 |
| 6 | 7.60 | 0.373 | 0.126 | 19.3 | 9.19 | 1.33 | 0.338 | >10 | >10 |
| 7 | 4.95 | 0.223 | 0.071 | 7.63 | 6.27 | 0.983 | 0.195 | >10 | >10 |
| 8 | 1.99 | 2.00 | 0.354 | 0.089 | 0.168 | 0.053 | 0.034 | 0.652 | 0.399 |
| 9 | 2.00 | 1.67 | 0.204 | 0.118 | 0.110 | 0.147 | 0.097 | 0.094 | 0.021 |
| 10 | 1.49 | 0.115 | 0.013 | 5.10 | 6.40 | 0.455 | 0.081 | >10 | >100 |
| 11 | 0.667 | 0.304 | 0.054 | 0.066 | n/a | 0.266 | 0.029 | 0.028 | 0.008 |
| 12 | 1.03 | 0.076 | 0.025 | 1.02 | n/a | 2.38 | 0.215 | 0.161 | 0.025 |

The invention claimed is:

1. A combination comprising roscovitine, or a pharmaceutically acceptable salt thereof, and methylprednisolone.

2. A pharmaceutical product comprising roscovitine, or a pharmaceutically acceptable salt thereof, and methylprednisolone as a combined preparation for simultaneous, sequential or separate use in therapy.

3. A pharmaceutical product according to claim 2 which further comprises a pharmaceutically acceptable carrier, diluent or excipient.

4. A method of treating systemic lupus erythematosis (SLE), the method comprising administering to a subject in need thereof a sufficient amount of a pharmaceutical product according to claim 2.

5. A method according to claim 4 wherein the roscovitine, or pharmaceutically acceptable salt thereof, and methylprednisolone are administered simultaneously, separately or sequentially.

6. A method according to claim 4 which comprises administering the roscovitine, or pharmaceutically acceptable salt thereof, to a subject prior to sequentially or separately administering methylprednisolone to said subject.

7. A method according to claim 4 which comprises administering methylprednisolone to a subject prior to sequentially or separately administering the roscovitine, or pharmaceutically acceptable salt thereof.

8. A method according to claim 4 wherein the roscovitine, or pharmaceutically acceptable salt thereof, and methylprednisolone are each administered in a therapeutically effective amount with respect to the individual components.

9. A method according to claim 4 wherein the roscovitine, or pharmaceutically acceptable salt thereof, and methylprednisolone are each administered in a subtherapeutic amount with respect to the individual components.

* * * * *